US012290462B2

(12) United States Patent
Blecher

(10) Patent No.: US 12,290,462 B2
(45) Date of Patent: *May 6, 2025

(54) ANATOMICAL BRACE FOR DYNAMICALLY STABILIZING THE ELBOW

(71) Applicant: Sports Medicine Sciences, LLC, Encino, CA (US)

(72) Inventor: Andrew Blecher, Encino, CA (US)

(73) Assignee: Sports Medicine Sciences, LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/239,196

(22) Filed: Aug. 29, 2023

(65) Prior Publication Data

US 2024/0130884 A1 Apr. 25, 2024
US 2024/0225880 A9 Jul. 11, 2024

Related U.S. Application Data

(63) Continuation of application No. 16/047,877, filed on Jul. 27, 2018, now Pat. No. 11,737,903.

(Continued)

(51) Int. Cl.
*A61F 5/00* (2006.01)
*A61F 5/01* (2006.01)
*A61F 5/058* (2006.01)

(52) U.S. Cl.
CPC ............ *A61F 5/013* (2013.01); *A61F 5/0118* (2013.01); *A61F 5/05858* (2013.01);
(Continued)

(58) Field of Classification Search
CPC ........ A61F 5/01; A61F 5/0102; A61F 5/0132; A61F 5/0125; A61F 5/013; A61F 5/0123;
(Continued)

(56) References Cited

U.S. PATENT DOCUMENTS 2,195,024 A 3/1940 Bullock
4,296,744 A 10/1981 Palumbo
(Continued)

FOREIGN PATENT DOCUMENTS

CA 2831507 4/2015
EP 2 727 565 5/2014
WO WO 2009/126724 10/2009

OTHER PUBLICATIONS

Bauerfeind USA Inc., Sports Elbow Brace, 2016, https://www.bauerfeind.com/b2c/Sports-Brace/Sports-Elbow-Brace/p/YPBF_BAE_EPITRPOWG.
(Continued)

*Primary Examiner* — Adam Baker
(74) *Attorney, Agent, or Firm* — Pandiscio & Pandiscio

(57) ABSTRACT

An anatomical brace for dynamically stabilizing the elbow during elbow articulation, the anatomical brace comprising: a brace body comprising a distal portion for fitting over the forearm of a user and a proximal portion for fitting over the upper arm of a user; a hinge mechanism comprising a distal segment, a proximal segment and a pivot for pivotally connecting the distal segment and the proximal segment, the distal segment of the hinge mechanism being mounted to the distal portion of the brace body and the proximal segment of the hinge mechanism being mounted to the proximal portion of the brace body; a pivot cable guide mounted to the anterior portion of the pivot; an upper arm cable guide mounted to at least one of the proximal segment of the hinge mechanism and the proximal portion of the brace body, the upper arm cable guide being configured to change the direction of a cable extending through the upper arm cable guide; an ulnar collateral ligament (UCL) cable guide mounted to the brace body and configured to direct a cable extending through the ulnar collateral ligament (UCL) cable guide over the ulnar collateral ligament (UCL) and toward (Continued)

the distal portion of the brace body; and a cable having a first end and a second end; the first end of the cable being mounted to the distal segment of the hinge mechanism, the second end of the cable being mounted to the distal portion of the brace body, and the cable being routed proximally along the distal segment of the hinge mechanism, through the pivot cable guide, proximally along the proximal segment of the hinge mechanism, through the upper arm cable guide, and through the ulnar collateral ligament (UCL) cable guide; wherein, when the anatomical brace is mounted to the arm of a user so that the distal portion of the brace body is secured to the forearm of the user, and the proximal portion of the brace body is secured to the upper arm of the user, and when the elbow thereafter moves to full extension, the cable is tensioned, whereby to apply a force to the ulnar collateral ligament (UCL) of the user, and when the elbow thereafter moves to full flexion, the cable is relaxed, so that the force applied to the ulnar collateral ligament (UCL) is released.

23 Claims, 17 Drawing Sheets

Related U.S. Application Data

(60) Provisional application No. 62/538,042, filed on Jul. 28, 2017.

(52) U.S. Cl.
CPC .............. *A61F 2005/0137* (2013.01); *A61F 2005/0158* (2013.01); *A61F 2005/0167* (2013.01); *A61F 2005/0181* (2013.01); *A61F 2005/0188* (2013.01)

(58) Field of Classification Search
CPC ...... A61F 5/3715; A61F 5/3723; A61F 5/373; A61F 2005/0165; A61F 2005/0169; A61F 2005/0167; A61F 2005/0158; A61F 2005/0155
USPC ............................. 602/5, 12, 16, 20, 21, 23
See application file for complete search history.

(56) References Cited

U.S. PATENT DOCUMENTS

| | | |
|---|---|---|
| 4,370,977 A | 2/1983 | Mauldin et al. |
| 4,370,978 A | 2/1983 | Palumbo |
| 4,397,308 A | 8/1983 | Hepburn |
| 4,423,720 A | 1/1984 | Meier et al. |
| 4,445,505 A | 5/1984 | Labour et al. |
| 4,489,718 A | 12/1984 | Martin |
| 4,508,111 A | 4/1985 | Hepburn |
| 4,607,628 A | 8/1986 | Dashefsky |
| 4,657,000 A | 4/1987 | Hepburn |
| 4,682,776 A | 7/1987 | Mitchell et al. |
| 4,733,656 A | 3/1988 | Marquette |
| 4,805,606 A | 2/1989 | McDavid, III |
| 4,856,500 A * | 8/1989 | Spademan ............ A61F 5/0125 602/26 |
| 5,002,045 A | 3/1991 | Spademan |
| 5,024,216 A | 6/1991 | Shiono |
| 5,112,045 A | 5/1992 | Mason et al. |
| 5,277,697 A | 1/1994 | France et al. |
| 5,303,716 A | 4/1994 | Mason et al. |
| 5,383,845 A | 1/1995 | Nebolon |
| 5,472,410 A | 12/1995 | Hamersly |
| 5,509,894 A | 4/1996 | Mason et al. |
| 5,562,605 A | 10/1996 | Taylor |
| 5,575,764 A | 11/1996 | Van Dyne |
| 5,599,288 A | 2/1997 | Shirley et al. |
| 5,613,943 A | 3/1997 | Palumbo |
| 5,624,390 A | 4/1997 | Van Dyne |
| 5,672,152 A | 9/1997 | Mason et al. |
| 5,683,353 A | 11/1997 | Hamersly |
| 5,759,167 A | 6/1998 | Shields, Jr. et al. |
| 5,772,618 A | 6/1998 | Mason et al. |
| 5,797,864 A | 8/1998 | Taylor |
| 5,807,294 A | 9/1998 | Cawley et al. |
| 5,827,208 A | 10/1998 | Mason et al. |
| 5,857,988 A | 1/1999 | Shirley |
| 5,865,776 A | 2/1999 | Springs |
| 6,001,075 A | 12/1999 | Clemens et al. |
| 6,110,138 A | 8/2000 | Shirley |
| 6,129,690 A | 10/2000 | Hamlin et al. |
| 6,245,034 B1 | 6/2001 | Bennett et al. |
| 6,287,269 B1 | 9/2001 | Osti et al. |
| 6,471,664 B1 | 10/2002 | Campbell et al. |
| 6,551,264 B1 | 4/2003 | Cawley et al. |
| 6,635,024 B2 | 10/2003 | Hatton et al. |
| 6,719,713 B2 | 4/2004 | Mason |
| 6,936,019 B2 | 8/2005 | Mason |
| 7,004,919 B2 | 2/2006 | Gaylord et al. |
| 7,059,329 B2 | 6/2006 | Mason et al. |
| 7,060,045 B2 | 6/2006 | Mason et al. |
| 7,083,586 B2 | 8/2006 | Simmons et al. |
| 7,146,651 B1 | 12/2006 | Lapin |
| 7,189,212 B2 | 3/2007 | Popp et al. |
| 7,192,407 B2 | 3/2007 | Seligman et al. |
| 7,207,960 B2 | 4/2007 | Kenney |
| 7,235,059 B2 | 6/2007 | Mason et al. |
| 7,479,122 B2 | 1/2009 | Ceriani et al. |
| 7,481,785 B2 | 1/2009 | Turrini et al. |
| 7,485,103 B2 | 2/2009 | Mason et al. |
| 7,517,330 B2 | 4/2009 | DeHarde et al. |
| 7,534,217 B2 | 5/2009 | Seligman et al. |
| 7,608,051 B1 * | 10/2009 | Nace .................. A61F 5/0123 602/5 |
| 7,811,242 B2 | 10/2010 | Seligman |
| 7,819,830 B2 | 10/2010 | Sindel et al. |
| 7,846,115 B2 | 12/2010 | Seligman et al. |
| 7,867,183 B2 | 1/2011 | Kazmierczak et al. |
| 7,905,851 B1 | 3/2011 | Bledsoe |
| 8,123,709 B2 | 2/2012 | DeHarde et al. |
| 8,172,781 B2 | 5/2012 | Oddou et al. |
| 8,273,045 B2 | 9/2012 | Ceriani |
| 8,277,403 B2 | 10/2012 | Ceriani et al. |
| 8,376,974 B2 | 2/2013 | Nace |
| 8,419,670 B2 | 4/2013 | Downing |
| 8,435,197 B2 | 5/2013 | Vollbrecht et al. |
| 8,882,688 B1 | 11/2014 | Ancinec |
| 8,945,031 B2 | 2/2015 | Cardinali |
| 9,095,418 B2 | 8/2015 | Cardinali et al. |
| 9,113,998 B2 | 8/2015 | Romo |
| 9,132,026 B2 | 9/2015 | Bledsoe et al. |
| 10,617,550 B2 | 4/2020 | Fedon et al. |
| 11,737,903 B2 * | 8/2023 | Blecher .............. A61F 5/05858 602/16 |
| 2002/0133108 A1 | 9/2002 | Jagodzinski |
| 2003/0144620 A1 | 7/2003 | Sieller et al. |
| 2008/0249448 A1 | 10/2008 | Stevenson et al. |
| 2011/0098618 A1 | 4/2011 | Fleming |
| 2011/0137220 A1 | 6/2011 | Vollbrecht et al. |
| 2013/0110020 A1 | 5/2013 | Ingimundarson et al. |
| 2013/0172797 A1 | 7/2013 | Merkley et al. |
| 2013/0245523 A1 | 9/2013 | Romo |
| 2014/0068838 A1 | 3/2014 | Beers et al. |
| 2014/0276305 A1 | 9/2014 | Cardinali et al. |
| 2014/0276311 A1 | 9/2014 | Hollister et al. |
| 2014/0298560 A1 | 10/2014 | Bailey, II et al. |
| 2014/0336554 A1 | 11/2014 | Romo et al. |
| 2015/0119777 A1 | 4/2015 | Garrish |
| 2015/0126917 A1 | 5/2015 | Stier |
| 2015/0133839 A1 | 5/2015 | Roebelt et al. |
| 2015/0374531 A1 | 12/2015 | Fedon |
| 2015/0374532 A1 | 12/2015 | Fedon |
| 2016/0256310 A1 | 9/2016 | Blecher |

OTHER PUBLICATIONS

(56) References Cited

OTHER PUBLICATIONS

Bellacure, Relieving pain. Restoring lifestyle., 2010, htttps://bellacure.com/en/products/index.html.
Breg, Inc., FreeRunner Knee Brace, 2016, http://www.breg.com/products/knee-bracing/patellofemoral/freerunner-knee-brace.
Breginc, https://www.youtube.com/watch?v=AARHoQ1xJXg&sns=em (published on Jul. 28, 2014).
Breginc, https://www.youtube.com/watch?v=FgBbbAjdSj4 (published on Jul. 30, 2012).
Breginc, https://www.youtube.com/watch?v=fr0Q5QKOO60 (published on Sep. 17, 2014).
Elastic definition, Dictionary.com, definition 1, https://www.dictionary.com/browse/elastic, 2020.
Stillwell, William, M.D., The VMO—The Key to Patella Tracking, Knee Pain Relief and Knee Joint Stability, EzineArticles, Nov. 24, 2008.

\* cited by examiner

ANATOMICAL BRACE FOR DYNAMICALLY STABILIZING THE ELBOW

REFERENCE TO PENDING PRIOR PATENT APPLICATION

This patent application claims benefit of U.S. Provisional Patent Application Ser. No. 62/538,042, filed Jul. 28, 2017 by Sports Medicine Sciences, LLC and Andrew Blecher for ANATOMICAL BRACE FOR DYNAMICALLY STABILIZING THE ELBOW, which patent application is hereby incorporated herein by reference.

FIELD OF THE INVENTION

This invention relates to anatomical braces in general, and more particularly to anatomical braces for dynamically stabilizing the elbow, especially during overhead throwing, other overhead activities and/or racquet sports, so as to protect the elbow from injury.

BACKGROUND OF THE INVENTION

Baseball players and other athletes are at risk of elbow injuries due to the valgus stresses on the ulnar collateral ligament (UCL) during elbow flexion (e.g., such as during the cocking and acceleration phases of throwing), and are also at risk of elbow injuries due to the snapping forces on the elbow from overextension (e.g., such as during the release and follow-through phases of throwing). See FIG. 1. These valgus stresses and snapping forces can lead to injuries such as ulnar collateral ligament (UCL) tears, growth plate injuries, stress fractures, chondral injuries and osteochondritis dessicans. All of these injuries may lead to pain, disability, decreased athletic performance, time missed from playing a sport and, in severe cases, career-ending surgery.

Conventional elbow braces are configured to provide a limit to the extension of the elbow, e.g., such as during the phases of throwing. By only providing a limit to the extension of the elbow during elbow movement (e.g., such as during the phases of throwing), conventional elbow braces do not provide support to the ulnar collateral ligament (UCL) during other phases of elbow motion (i.e., conventional elbow braces do not provide variable tension as the wearer moves their arm, such as during throwing). Therefore an individual wearing a conventional elbow brace is still at risk of elbow injuries due to the valgus stresses on the ulnar collateral ligament (UCL) during elbow flexion (e.g., such as during the cocking and acceleration phases of throwing).

Thus there is a need for an elbow brace that provides a dynamically adjustable force to protect the elbow from forces that may cause injury during all of the phases of elbow motion, e.g., such as during all of the phases of throwing. The elbow brace must be comfortable and low-profile so as to prevent disruption of the mechanics of the elbow during a throwing motion (or other motion) so that the elbow brace does not affect the performance of a wearer.

SUMMARY OF THE INVENTION

The present invention comprises the provision and use of a novel anatomical brace for dynamically stabilizing the elbow, especially during overhead throwing, other overhead activities and/or racquet sports, so as to protect the elbow from injury.

Among other things, the novel anatomical brace provides a dynamically adjustable force to protect the elbow from forces that may cause injury during all of the phases of elbow motion, e.g., such as during all of the phases of throwing. And the novel anatomical brace is configured to be comfortable and low-profile so as to prevent disruption of the mechanics of the elbow during a throwing motion (or other motion) so that the elbow brace does not affect the performance of a wearer.

In one form of the invention, there is provided an anatomical brace for dynamically stabilizing the elbow during elbow articulation, said anatomical brace comprising:
a brace body comprising a distal portion for fitting over the forearm of a user and a proximal portion for fitting over the upper arm of a user;
a hinge mechanism comprising a distal segment, a proximal segment and a pivot for pivotally connecting said distal segment and said proximal segment, said distal segment of said hinge mechanism being mounted to said distal portion of said brace body and said proximal segment of said hinge mechanism being mounted to said proximal portion of said brace body;
a pivot cable guide mounted to the anterior portion of said pivot;
an upper arm cable guide mounted to at least one of said proximal segment of said hinge mechanism and said proximal portion of said brace body, said upper arm cable guide being configured to change the direction of a cable extending through said upper arm cable guide;
an ulnar collateral ligament (UCL) cable guide mounted to said brace body and configured to direct a cable extending through said ulnar collateral ligament (UCL) cable guide over the ulnar collateral ligament (UCL) and toward said distal portion of said brace body; and
a cable having a first end and a second end;
said first end of said cable being mounted to said distal segment of said hinge mechanism, said second end of said cable being mounted to said distal portion of said brace body, and said cable being routed proximally along said distal segment of said hinge mechanism, through said pivot cable guide, proximally along said proximal segment of said hinge mechanism, through said upper arm cable guide, and through said ulnar collateral ligament (UCL) cable guide;
wherein, when said anatomical brace is mounted to the arm of a user so that said distal portion of said brace body is secured to the forearm of the user, and said proximal portion of said brace body is secured to the upper arm of the user, and when the elbow thereafter moves to full extension, said cable is tensioned, whereby to apply a force to the ulnar collateral ligament (UCL) of the user, and when the elbow thereafter moves to full flexion, said cable is relaxed, so that the force applied to the ulnar collateral ligament (UCL) is released.

In another form of the invention, there is provided an anatomical brace for dynamically stabilizing the elbow during elbow articulation, said anatomical brace comprising:
a brace body comprising a distal portion for fitting over the forearm of a user and a proximal portion for fitting over the upper arm of a user;
a hinge mechanism comprising a distal segment, a proximal segment and a pivot for pivotally connecting said distal segment and said proximal segment, said distal segment of said hinge mechanism being mounted to said distal portion of said brace body and said proximal segment of said hinge mechanism being mounted to said proximal portion of said brace body;

a pivot cable guide mounted to the posterior portion of said pivot;

an upper arm cable guide mounted to at least one of said proximal segment of said hinge mechanism and said proximal portion of said brace body, said upper arm cable guide being configured to change the direction of a cable extending through said upper arm cable guide;

an ulnar collateral ligament (UCL) cable guide mounted to said brace body and configured to direct a cable extending through said ulnar collateral ligament (UCL) cable guide over the ulnar collateral ligament (UCL) and toward said distal portion of said brace body;

a cable having a first end and a second end;

said first end of said cable being mounted to said distal segment of said hinge mechanism, said second end of said cable being mounted to said distal portion of said brace body, and said cable being routed proximally along said distal segment of said proximally along said proximal segment of said hinge mechanism, through said upper arm cable guide, and through said ulnar collateral ligament (UCL) cable guide;

a limiter cable guide mounted to the anterior portion of said pivot; and a limiter cable having a first end and a second end;

said first end of said limiter cable being mounted to said distal segment of said hinge mechanism, said second end of said limiter cable being mounted to said proximal segment of said hinge mechanism, and said limiter cable being routed through said limiter cable guide;

wherein, when said anatomical brace is mounted to the arm of a user so that said distal portion of said brace body is secured to the forearm of the user, and said proximal portion of said brace body is secured to the upper arm of the user, and when the elbow thereafter moves to full extension, said cable is tensioned, whereby to apply a force to the ulnar collateral ligament (UCL) of the user, and when the elbow thereafter moves to full flexion, said cable is relaxed, so that the force applied to the ulnar collateral ligament (UCL) is released.

In another form of the invention, there is provided a method for dynamically stabilizing the elbow during elbow articulation, said method comprising:

providing an anatomical brace, said anatomical brace comprising:
  a brace body comprising a distal portion for fitting over the forearm of a user and a proximal portion for fitting over the upper arm of a user;
  a hinge mechanism comprising a distal segment, a proximal segment and a pivot for pivotally connecting said distal segment and said proximal segment, said distal segment of said hinge mechanism being mounted to said distal portion of said brace body and said proximal segment of said hinge mechanism being mounted to said proximal portion of said brace body;
  a pivot cable guide mounted to the anterior portion of said pivot;
  an upper arm cable guide mounted to at least one of said proximal segment of said hinge mechanism and said proximal portion of said brace body, said upper arm cable guide being configured to change the direction of a cable extending through said upper arm cable guide;
  an ulnar collateral ligament (UCL) cable guide mounted to said brace body and configured to direct a cable extending through said ulnar collateral ligament (UCL) cable guide over the ulnar collateral ligament (UCL) and toward said distal portion of said brace body; and
  a cable having a first end and a second end;
  said first end of said cable being mounted to said distal segment of said hinge mechanism, said second end of said cable being mounted to said distal portion of said brace body, and said cable being routed proximally along said distal segment of said proximally along said proximal segment of said hinge mechanism, through said upper arm cable guide, and through said ulnar collateral ligament (UCL) cable guide;
  wherein, when said anatomical brace is mounted to the arm of a user so that said distal portion of said brace body is secured to the forearm of the user, and said proximal portion of said brace body is secured to the upper arm of the user, and when the elbow thereafter moves to full extension, said cable is tensioned, whereby to apply a force to the ulnar collateral ligament (UCL) of the user, and when the elbow thereafter moves to full flexion, said cable is relaxed, so that the force applied to the ulnar collateral ligament (UCL) is released;

fitting said distal portion of said brace body over the forearm of a user and said proximal portion of said brace body over the upper arm of a user;

positioning said first end of said cable to said distal segment of said hinge mechanism, and positioning said second end of said cable to said distal portion of said brace body; and articulating the elbow.

In another form of the invention, there is provided a method for dynamically stabilizing the elbow during elbow articulation, said method comprising:

providing an anatomical brace, said anatomical brace comprising:
  a brace body comprising a distal portion for fitting over the forearm of a user and a proximal portion for fitting over the upper arm of a user;
  a hinge mechanism comprising a distal segment, a proximal segment and a pivot for pivotally connecting said distal segment and said proximal segment, said distal segment of said hinge mechanism being mounted to said distal portion of said brace body and said proximal segment of said hinge mechanism being mounted to said proximal portion of said brace body;
  a pivot cable guide mounted to the posterior portion of said pivot;
  an upper arm cable guide mounted to at least one of said proximal segment of said hinge mechanism and said proximal portion of said brace body, said upper arm cable guide being configured to change the direction of a cable extending through said upper arm cable guide;
  an ulnar collateral ligament (UCL) cable guide mounted to said brace body and configured to direct a cable extending through said ulnar collateral ligament (UCL) cable guide over the ulnar collateral ligament (UCL) and toward said distal portion of said brace body;
  a cable having a first end and a second end;

said first end of said cable being mounted to said distal segment of said hinge mechanism, said second end of said cable being mounted to said distal portion of said brace body, and said cable being routed proximally along said distal segment of said proximally along said proximal segment of said hinge mechanism, through said upper arm cable guide, and through said ulnar collateral ligament (UCL) cable guide;

a limiter cable guide mounted to the anterior portion of said pivot; and a limiter cable having a first end and a second end;

said first end of said limiter cable being mounted to said distal segment of said hinge mechanism, said second end of said limiter cable being mounted to said proximal segment of said hinge mechanism, and said limiter cable being routed through said limiter cable guide;

wherein, when said anatomical brace is mounted to the arm of a user so that said distal portion of said brace body is secured to the forearm of the user, and said proximal portion of said brace body is secured to the upper arm of the user, and when the elbow thereafter moves to full extension, said cable is tensioned, whereby to apply a force to the ulnar collateral ligament (UCL) of the user, and when the elbow thereafter moves to full flexion, said cable is relaxed, so that the force applied to the ulnar collateral ligament (UCL) is released;

fitting said distal portion of said brace body over the forearm of a user and said proximal portion of said brace body over the upper arm of a user;

positioning said first end of said cable to said distal segment of said hinge mechanism, and positioning said second end of said cable to said distal portion of said brace body, and positioning said first end of said limiter cable to said distal segment of said hinge mechanism, and positioning said second end of said limiter cable to said proximal segment of said hinge mechanism; and articulating the elbow.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
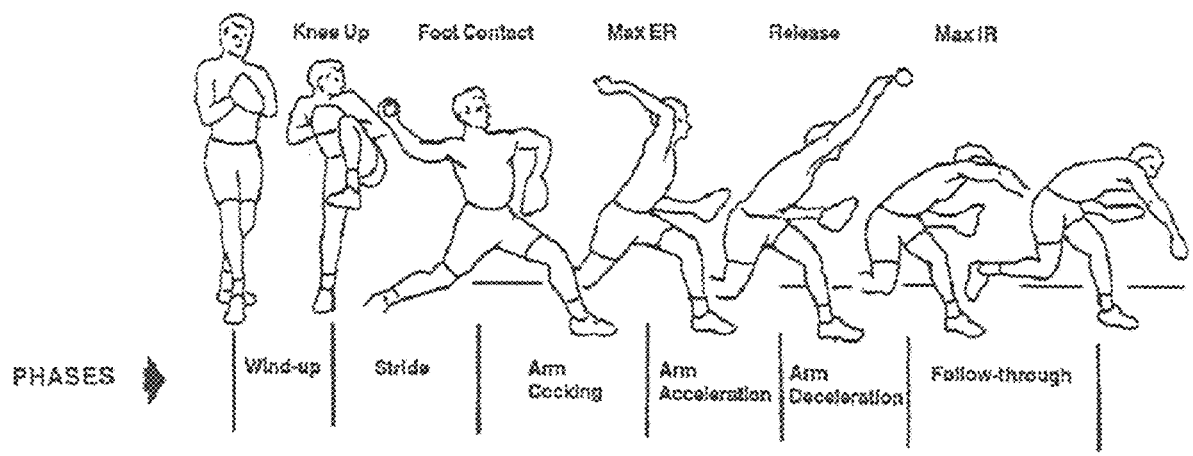
FIG. 1 is a schematic view showing the phases of throwing.
Figure 2:
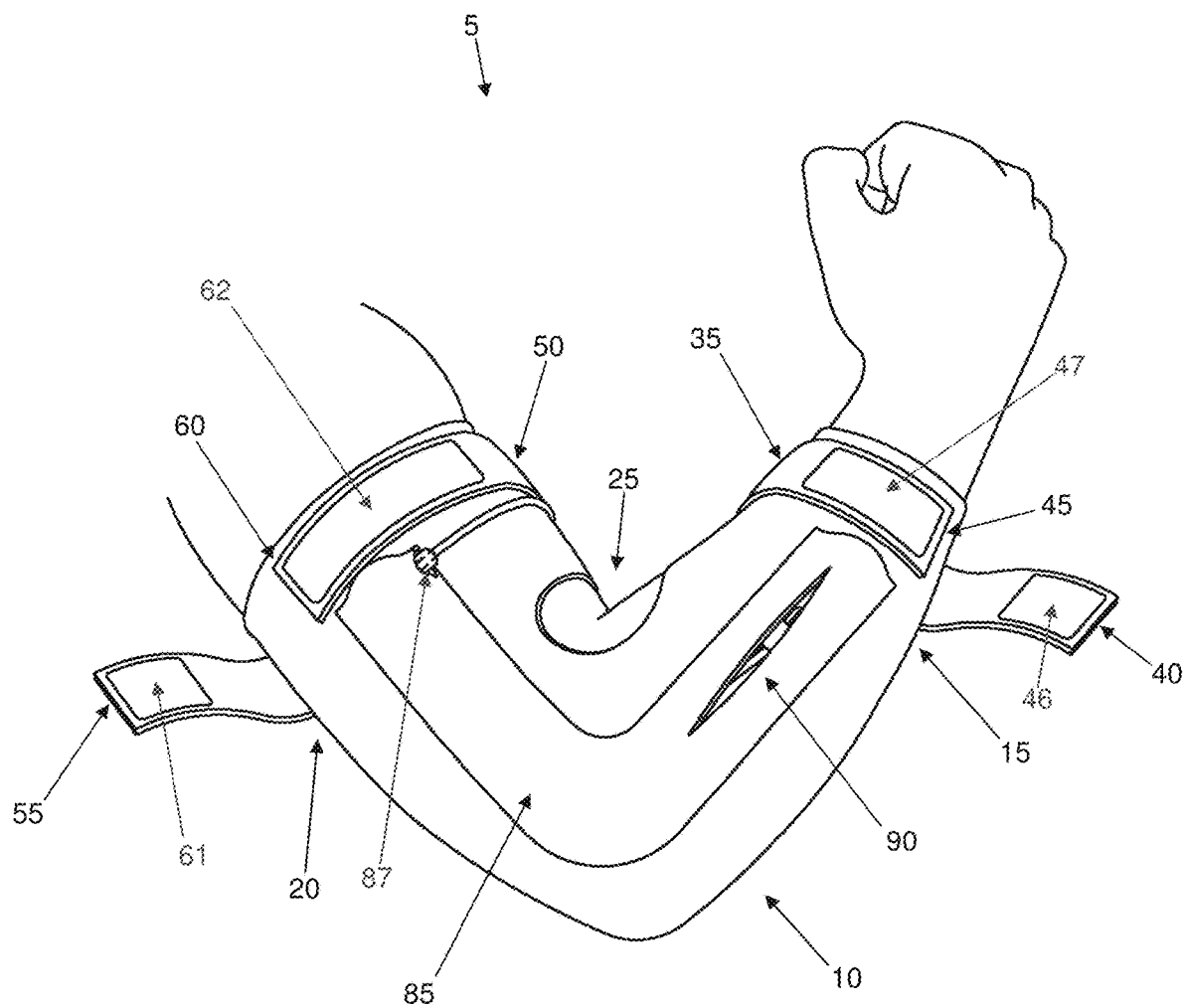
FIGS. 2-7 are schematic views showing an anatomical brace formed in accordance with the present invention.
Figure 3:
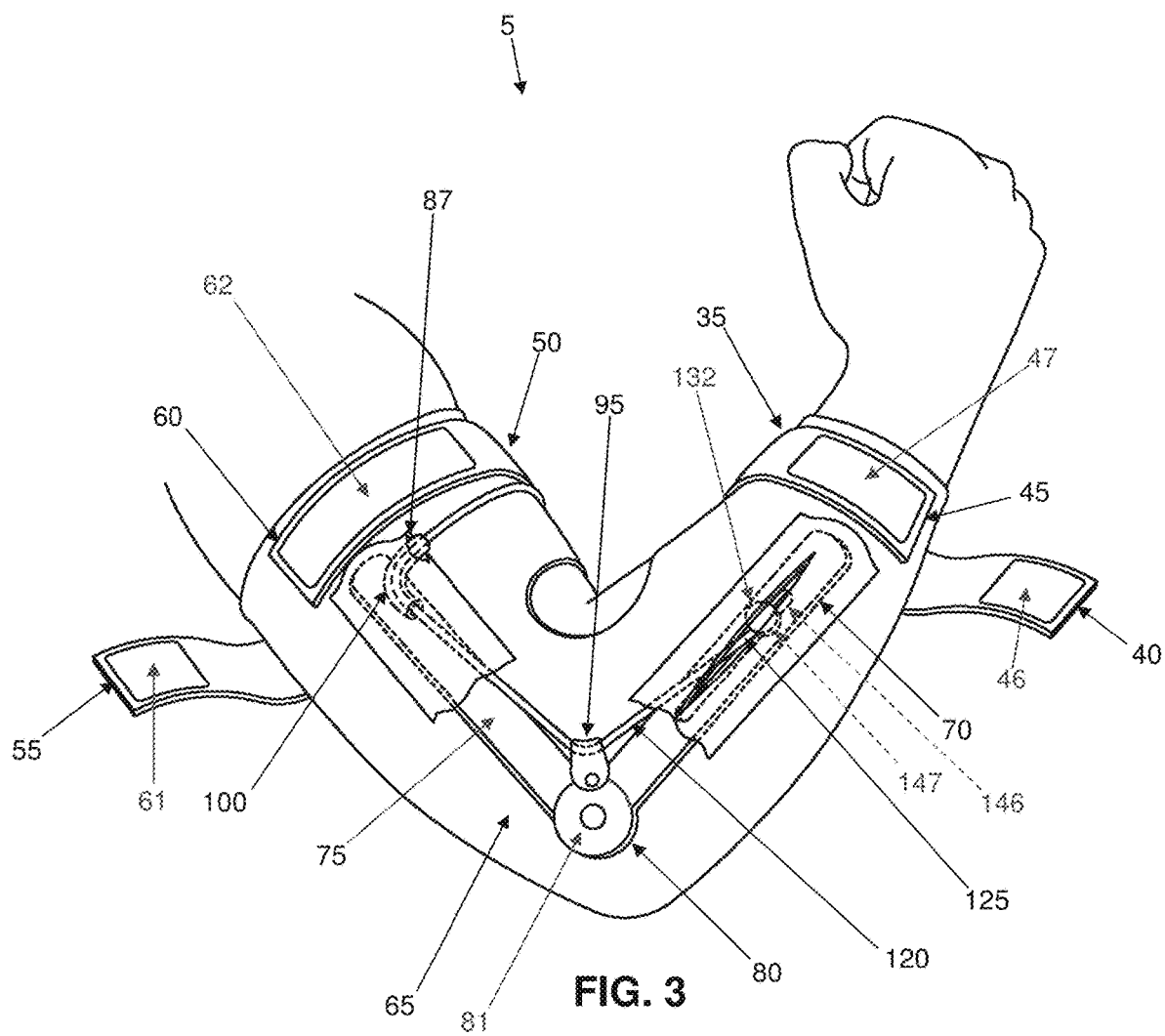
Figure 4:
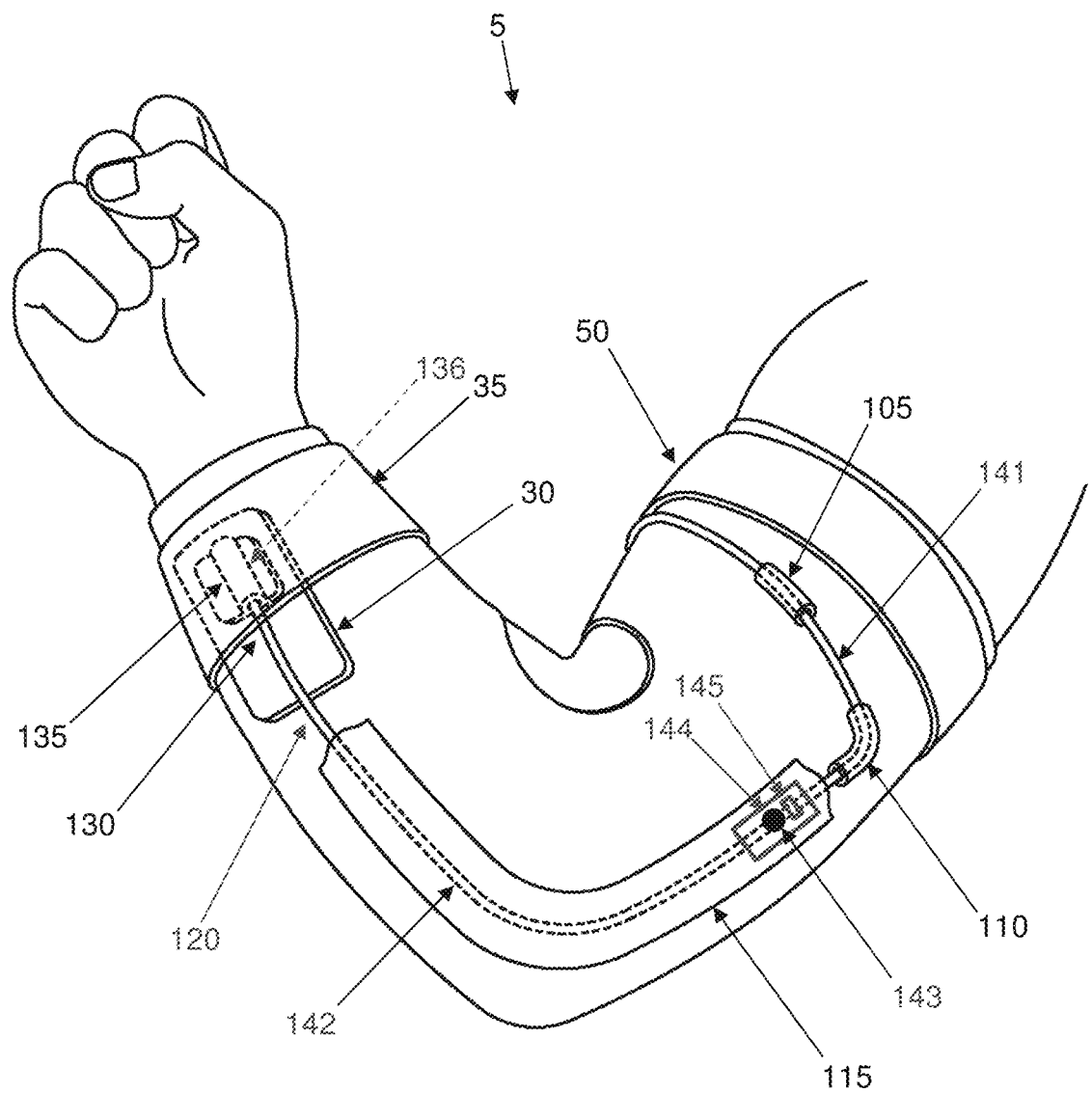
Figure 5:
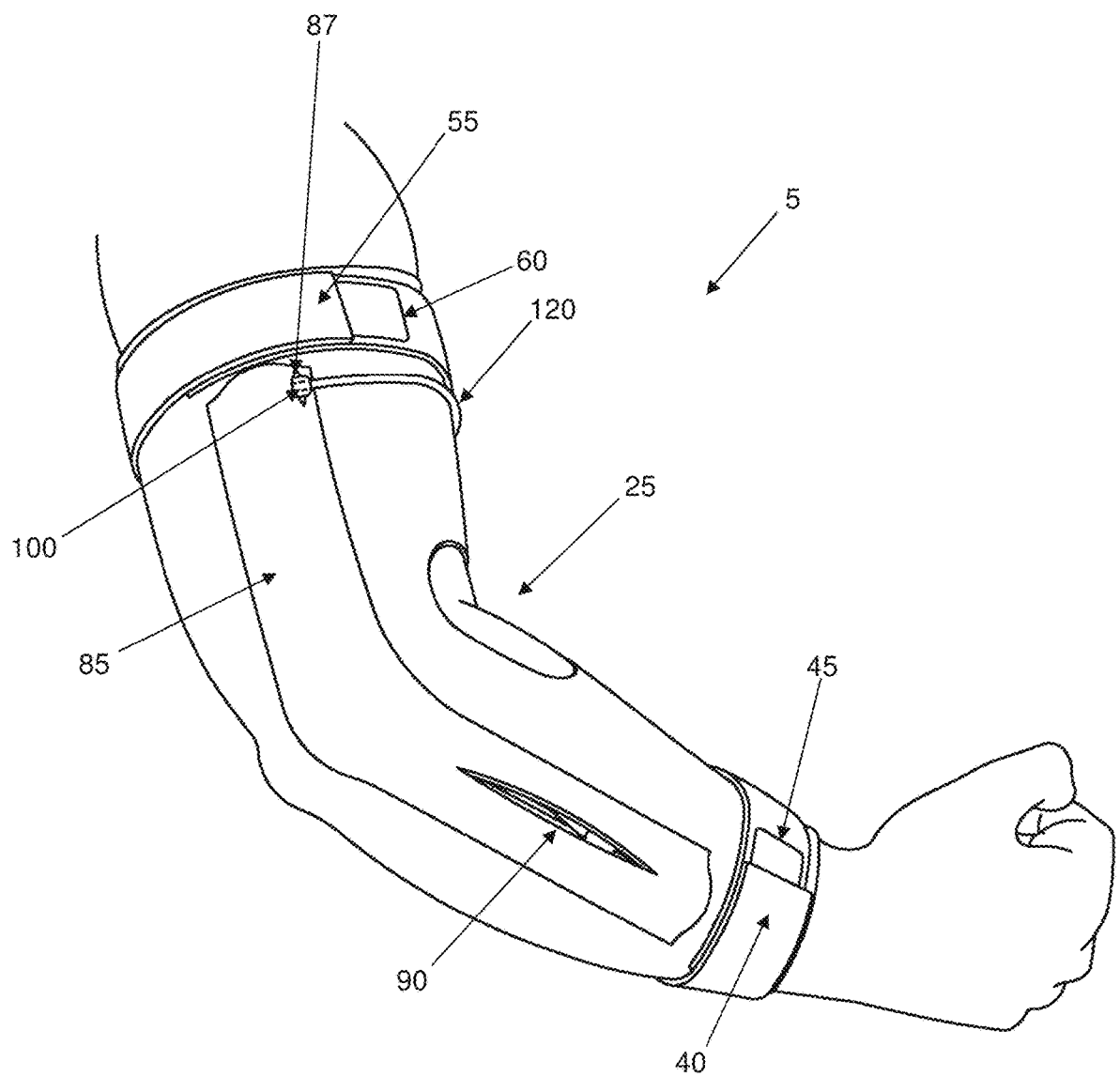
Figure 6:
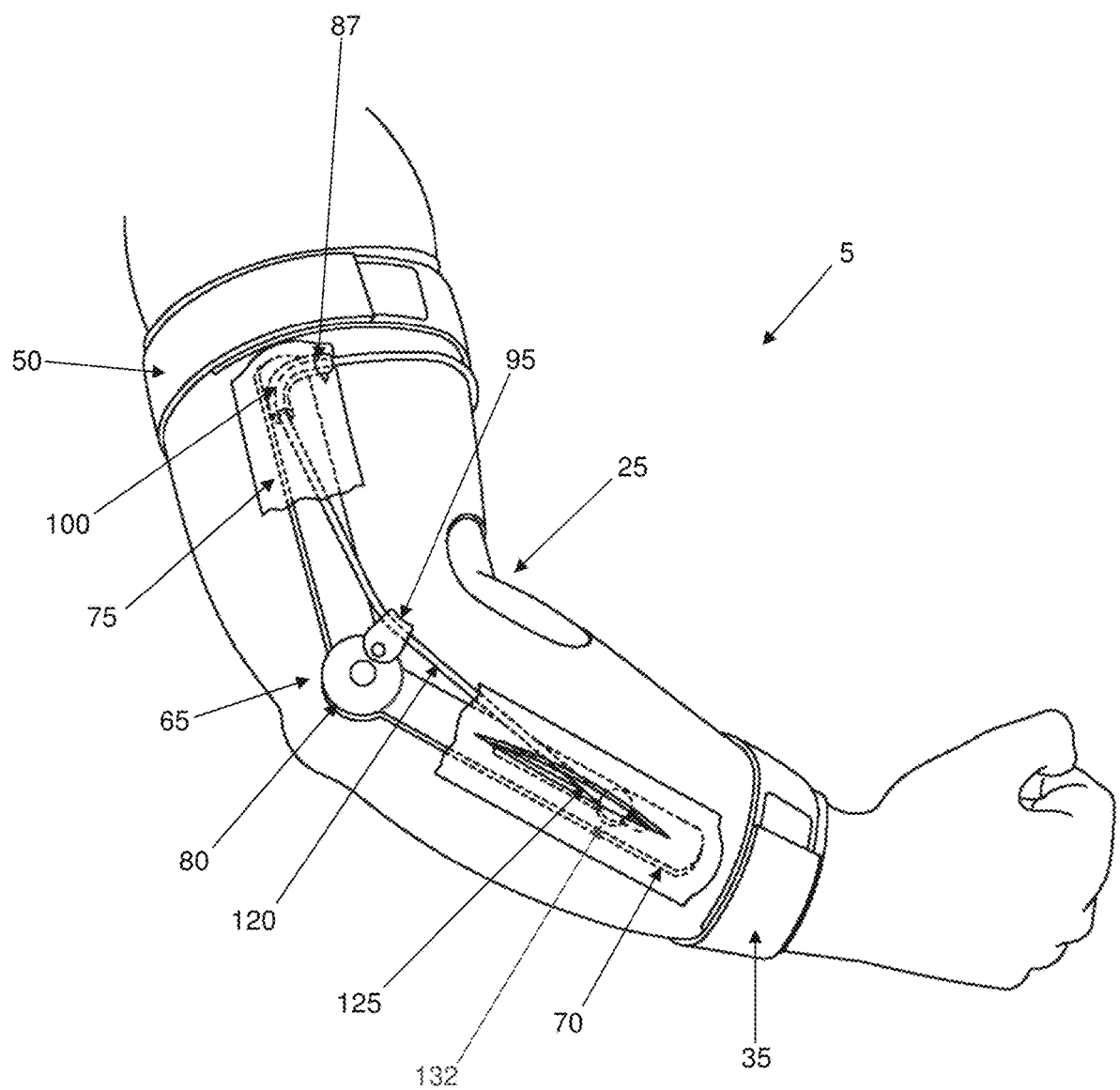

The present invention comprises the provision and use of a novel anatomical brace for dynamically stabilizing the elbow, especially during overhead throwing, other overhead activities and/or racquet sports, so as to protect the elbow from injury.

Among other things, the novel anatomical brace provides a dynamically adjustable force to protect the elbow from forces that may cause injury during all of the phases of elbow motion, e.g., such as during all of the phases of throwing. And the novel anatomical brace is configured to be comfortable and low-profile so as to prevent disruption of the mechanics of the elbow during a throwing motion (or other motion) so that the elbow brace does not affect the performance of a wearer.

Construction of the Novel Anatomical Brace

Looking first at FIGS. 2-7, in one preferred form of the invention, there is provided a novel anatomical brace 5 for dynamically stabilizing the elbow during overhead throwing so as to protect the elbow from injury. Anatomical brace 5 generally comprises a brace body 10 comprising a distal portion 15, a proximal portion 20, a central opening 25 and one half 30 (FIG. 4) of a hook-and-mesh (e.g., Velcro®) fastener. Brace body 10 is flexible, and is preferably formed out of a flexible material such as a woven fabric, a synthetic rubber, etc. In one preferred form of the invention, brace body 10 is an elbow sleeve formed out of a breathable lightweight elastic fabric which provides light compression to the forearm, elbow and upper arm of the user.

A distal strap 35 (FIG. 3), having a first end 40 and a second end 45, is mounted on distal portion 15 of brace body 10 and is configured to be secured around the forearm of a wearer so as to adjustably fasten brace body 10 to the forearm of a wearer. One half 46 of a hook-and-mesh (e.g., Velcro®) fastener is fixed to the first end 40 of distal strap 35, and the other half 47 of a hook-and-mesh (e.g., Velcro®) fastener is fixed to second end 45 of distal strap 35, such that distal strap 35 can be wrapped over distal portion 15 of brace body 10 and secured in place, whereby to secure distal portion 15 of brace body 10 to the forearm of the user.

A proximal strap 50 (FIG. 3), having a first end 55 and a second end 60, is mounted on proximal portion 20 of brace body 10 and is configured to be secured around the bicep area of the wearer so as to adjustably fasten brace body 10 to the arm of a wearer. One half 61 of a hook-and-mesh (e.g., Velcro®) fastener is fixed to first end 55 of proximal strap 50, and the other half 62 of a hook-and-mesh (e.g., Velcro®) fastener is fixed to second end 60 of proximal strap 50, such that proximal strap 50 can be wrapped over proximal portion 20 of brace body 10 and secured in place, whereby to secure proximal portion 20 of brace body 10 to the upper arm of the wearer.

Central opening 25 (FIG. 3) of brace body 10 is configured to be positioned in the antecubital area (i.e., the front crease of the elbow) of a wearer so that the material of brace body 10 does not bunch when the elbow is flexed (which could inhibit flexing of the elbow).

A hinge mechanism 65 is mounted on the lateral portion of brace body 10 (i.e., on the radial side of the elbow). More particularly, hinge mechanism 65 comprises a distal segment 70 and a proximal segment 75, with distal segment 70 being connected to proximal segment 75 at a pivot 80. Distal segment 70 of hinge mechanism 65, and proximal segment 75 of hinge mechanism 65, are each relatively stiff but have some degree of flexibility, and are preferably formed out of a plastic, or a carbon fiber, or a lightweight metal, etc. Pivot 80 of hinge mechanism 65 is relatively frictionless (i.e., it is easily articulated) and is preferably formed as an assembly comprising a central disc-shaped body 81 (FIG. 3) to which both distal segment 70 and proximal segment 75 are pivotally attached. Alternatively, pivot 80 can comprise a simple "rivet pivot" or "screw pivot" of the sort well known in the art where distal segment 70 and proximal segment 75 pivotally articulate relative to one another.

In one preferred form of the invention, hinge mechanism 65 comprises an articulatable plastic structure and is sewn into brace body 10 on the radial side of the elbow.

It should be appreciated that the configuration of hinge mechanism 65 is preferably low profile so as to prevent disruption of the mechanics of the elbow during a throwing motion (or other motion) so that the elbow brace does not affect the movements of a wearer when flexing or extending the elbow.

A cover 85 (FIG. 2) is preferably mounted over hinge mechanism 65 so as to shield hinge mechanism 65 from inadvertently catching on clothing, etc. Cover 85 preferably comprises an opening 87 (FIG. 2) on the proximal portion of cover 85 and a slit 90 over distal segment 70 of hinge mechanism 65. In one preferred form of the invention, cover 85 may be formed out of the same material as brace body 10, or cover 85 may be formed out of a different material than brace body 10. In one preferred form of the invention, cover 85 is sewn onto brace body 10. It should be appreciated that opening 87 of cover 85 is configured to allow a cable (see below) to pass through cover 85, and slit 90 of cover 85 is configured to allow access to the interior of cover 85, and hence access to distal segment 70 of hinge mechanism 65.

In an alternative form of the invention, cover 85 is removably mounted to brace body 10, e.g., via one or more hook-and-mesh (e.g., Velcro®) fasteners, so as to selectively cover/uncover hinge mechanism 65.

A first cable guide (e.g., a pivot guide) 95 (FIG. 3) is mounted to pivot 80 on the lateral portion of anatomical brace 5.

A second cable guide (e.g., a brace tunnel) 100 (FIG. 3) is mounted to proximal segment 75 of hinge mechanism 65, also on the lateral portion of anatomical brace 5. Where second cable guide 100 comprises a brace tunnel, the brace tunnel may be formed out of the same material as brace body 10, or the brace tunnel may be formed out of a different material than brace body 10. In one preferred form of the invention, second cable guide 100 forms a 90 degree angle. It will be appreciated that in one preferred form of the invention, second cable guide 100 is partially covered by cover 85, with a portion of second cable guide 100 protruding from opening 87 of cover 85.

A third cable guide (e.g., a brace tunnel) 105 (FIG. 4) is mounted to proximal portion 20 of brace body 10 on the medial portion of anatomical brace 5. Where third cable guide 105 comprises a brace tunnel, the brace tunnel may be formed out of the same material as brace body 10, or the brace tunnel may be formed out of a different material than brace body 10.

A fourth cable guide (e.g., a brace tunnel) 110 (FIG. 4) is mounted to proximal portion 20 of brace body 10, also on the medial portion of anatomical brace 5. Where fourth cable guide 110 comprises a brace tunnel, the brace tunnel may be formed out of the same material as brace body 10, or the brace tunnel may be formed out of a different material than brace body 10. In one preferred form of the invention, fourth cable guide 110 forms a 90 degree angle.

A fifth cable guide (e.g., a brace tunnel) 115 (FIG. 4) is mounted to brace body 10, also on the medial portion of anatomical brace 5, and extends over the ulnar collateral ligament (UCL). Where fifth cable guide 115 comprises a brace tunnel, the brace tunnel may be formed out of the same material as brace body 10, or the brace tunnel may be formed out of a different material than brace body 10. In one preferred form of the invention, fifth cable guide 115 comprises a fabric which is sewn onto brace body 10.

A cable 120 (FIGS. 3 and 4) runs along hinge mechanism 65, crosses over the biceps or triceps of the wearer, and then over the ulnar collateral ligament (UCL) of the wearer to the forearm of the wearer, so that cable 120 tightens during elbow extension and relaxes during elbow flexion. More particularly, cable 120 comprises a first end 125 (FIG. 3) which is adjustably secured to distal segment 70 of hinge mechanism 65, and a second end 130 (FIG. 4) which is adjustably secured (see below) to the medial distal portion 15 of brace body 10 (see below), with the intermediate portion of cable 120 extending proximally along hinge mechanism 65, through first cable guide 95 (FIG. 3), proximally along proximal segment 75 of hinge mechanism 65, through second cable guide 100 (FIG. 3), across the biceps or triceps of the wearer, through third cable guide 105 (FIG. 4), through fourth cable guide 110 (FIG. 4), and then through fifth cable guide 115 (FIG. 4), with cable 120 passing over the ulnar collateral ligament (UCL).

First end 125 of cable 120 is preferably adjustably fixed to distal segment 70 of hinge mechanism 65 via an adjustable sliding termination point 132 (FIG. 3), and second end 130 of cable 120 is preferably adjustably fixed to a termination point 135 on distal portion 15 of brace body 10, e.g., via the other half 136 of a hook-and-mesh (e.g., Velcro®) fastener which mates to the aforementioned one half 30 of a hook-and-mesh (e.g., Velcro®) fastener.

In other words:
- one end of cable 120 is adjustably fixed to distal segment 70 of hinge mechanism 65;
- the body of cable 120 passes proximally along distal segment 70 of hinge mechanism 65, through first cable guide 95 on the flexion side of pivot 80, proximally along proximal segment 75 of hinge mechanism 65, enters second cable guide 100 and is redirected 90 degrees so as to pass laterally across the anterior biceps area to the opposite side of the arm (i.e., to the ulnar side of the arm), through third cable guide 105, enters fourth cable guide 110 and is redirected 90 degrees so as to pass distally back down the medial side of brace body 10, enters fifth cable guide 115 so that cable 120 is passed over the ulnar collateral ligament (UCL); and exits fifth cable guide 115 extending distally along the forearm; and
- the second end of cable 120 is adjustably fixed to distal portion 15 of brace body 10. Specifically, as cable 120 passes through fifth cable guide 115, cable 120 travels along the ulnar side of the elbow, overlaying the region where the ulnar collateral ligament (UCL) is located.

By virtue of this construction, and as will hereinafter be discussed in further detail, cable 120 is able to release tension when the elbow flexes and increase tension when the elbow extends. Furthermore, when cable 120 is tensioned, cable 120 applies a supportive compression to the ulnar collateral ligament (UCL). Thus it will be seen that the present invention provides a hinged elbow brace with a cable system where the cable passes along the length of the hinge, on one side of the hinge pivot, and with the cable overlying the ulnar collateral ligament (UCL). This unique design allows for tightening of the cable during elbow extension so as to protect the elbow joint by limiting overextension of the joint and by providing support to the ulnar collateral ligament (UCL) during elbow extension; and provides for loosening of the cable during elbow flexion.

In one preferred form of the invention, cable 120 comprises a non-elastic first segment 141 which includes the aforementioned first end 125, and an elastic second segment 142 which includes the aforementioned second end 130. First segment 141 transitions to second segment 142 at a transition zone 143. In one preferred form of the invention, non-elastic first segment 141 comprises a non-stretchable metal or plastic cable. And in one preferred form of the invention, elastic second segment 142 comprises an elastomeric cord or other elastically-stretchable element.

Significantly, where cable 120 comprises a non-elastic first segment 141 and an elastic second segment 142, cable 120 (and specifically elastic second segment 142 of cable 120) provides variable tension as the wearer flexes and extends their elbow, i.e., elastic second segment 142 of cable 120 provides increasing elastic tension as the elbow extends (and the tension on cable 120 is increased) and decreasing elastic tension as the elbow flexes (and the tension in cable 120 is decreased). Also significantly, elastic second segment 142 of cable 120 provides increasing tension over the ulnar collateral ligament (UCL) as the elbow extends, thereby providing increased support to the ulnar collateral ligament (UCL) during elbow extension.

In one preferred form of the invention, a connector 144 (FIG. 4) is disposed at transition zone 143 so as to secure first segment 141 of cable 120 to second segment 142 of cable 120. This arrangement is desirable since it allows one second segment 142 (comprising a specific degree of elasticity and/or a specific tensile strength) to be replaced by another second segment 142 (comprising a different degree of elasticity and/or a different tensile strength). In this way, users having different physical attributes (e.g., different physical characteristics, different physical strengths, etc.) can select a particular second segment 142 to create a complete cable 120 having the desired characteristics.

And in one preferred form of the invention, connector 144 can include a tension sensor 145 for detecting and reporting the tension occurring at transition zone 143. By way of example but not limitation, tension sensor 145 at connector 144 can be a tension sensor of the sort configured to detect and wirelessly report (e.g., via Bluetooth, WiFi, etc.) the tension occurring at transition zone 143 to a remote unit, e.g., a smartphone, a smartwatch, a tablet, a laptop, etc., where the smartphone, smartwatch, tablet, laptop, etc. is running an applet for assessing and displaying information relating to the tension detected at transition zone 143. In one preferred form of the invention, the smartphone, smartwatch, tablet, laptop, etc. is connected to the internet via a cellular and/or WiFi communication link to enable uploading of the information relating to the tension detected by tension sensor 145 at transition zone 143.

The ability to monitor the tension occurring at transition zone 143 of cable 120 can be highly advantageous, since as the user's muscles fatigue, the user is able to provide less support for the joint, so that tension at transition zone 143 increases. Therefore, increasing tension at transition zone 143 is indicative of increasing muscle fatigue in the user, which can be important for deciding when to stop or reduce joint flexing (e.g., in the case of a baseball pitcher, when to take the pitcher out of the game).

If desired, tension sensor 145 can be disposed at a location other than connector 144, e.g., tension sensor 145 can be mounted to another part of cable 120 (e.g., tension sensor 145 can be mounted to non-elastic first segment 141 of cable 120, or tension sensor 145 can be mounted to elastic second segment 142 of cable 120), or tension sensor 145 can be mounted at the point at which non-elastic first segment 141 is secured to distal segment 70 of hinge mechanism 65, or tension sensor 145 can be mounted at the point at which elastic second segment 142 is secured to distal portion 15 of brace body 10, etc.

The adjustable nature of the elasticity of the length of second segment 142 of cable 120, as well as the adjustable securement points of first end 125 and second end 130 of cable 120 on brace body 10, allows for the optimal amount of dynamically-adjustable tension to be established in anatomical brace 5 during extension of the elbow.

It should be appreciated that first end 125 of cable 120 is adjustably mounted to distal segment 70 of hinge mechanism 65 such that the position of first end 125 of cable 120 can be adjusted relative to distal segment 70 of hinge mechanism 65, whereby to change the angle and/or tension of cable 120, in order to accommodate a wearer's anatomy. In one preferred form of the invention, first end 125 of cable 120 is adjustably mounted to distal segment 70 of hinge mechanism 65 using a rail, with an adjustable fixation element (e.g., a set screw) being used to lock first end 125 of cable 120 in place at a desired position along the rail. More particularly, in this form of the invention, distal segment 70 of hinge mechanism 65 comprises a rail 146, and first end 125 of cable 120 is mounted to an adjustable fixation element (e.g., a set screw) 147—adjustable fixation element (e.g., set screw) 147 is slid along rail 146 until first end 125 of cable 120 is at a desired location relative to distal segment 70 of hinge mechanism 65, and then adjustable fixation element (e.g., set screw) 147 is locked in position on rail 146.

It should also be appreciated that second end 130 of cable 120 is adjustably mounted to termination point 135 on the medial distal portion 15 of brace body 10 such that the position of second end 130 of cable 120 can be adjusted relative to medial distal portion 15 of brace body 10, whereby to change the angle and/or tension of cable 120, in order to accommodate the wearer's anatomy. In one preferred form of the invention, second end 130 of cable 120 is adjustably mounted to termination point 135 using a hook-and-mesh (e.g., Velcro®) fastener. By way of example but not limitation, one half 136 of a hook-and-mesh (e.g., Velcro®) fastener is fixed to second end 130 of cable 120 and the other half 30 of a hook-and-mesh (e.g., Velcro®) fastener is mounted to distal portion 15 of brace body 10 as previously described.

It should be appreciated that many other mounting mechanisms (e.g., snap fasteners, cable clamps, cable tie-downs, etc.) may be used to adjustably mount the two ends of cable 120 to the remainder of the brace.

Use of the Novel Anatomical Brace

In use, and still looking at FIGS. 2-7, anatomical brace 5 is first secured to a wearer by positioning brace body 10 over the elbow so that central opening 25 of brace body 10 is in the antecubital area (i.e., the front crease of the elbow) of the wearer. Note that when anatomical brace 5 is positioned in this manner about the elbow of a wearer, hinge mechanism 65 will extend along the lateral portion of the elbow, and the interior of the elbow is left substantially uncovered by anatomical brace 5. And note also that no hinge mechanism is disposed along the medial portion of the elbow.

Next, cable 120 has its first end 125 adjustably secured to the lateral portion of distal segment 70 of hinge mechanism 65, and second end 130 of cable 120 is adjustably secured to the medial portion of distal portion 15 of brace body 10, with tension being adjusted as appropriate.

Distal strap 35 is then wrapped around the forearm portion of brace body 10, overlapping the joined first half 30 and second half 136 of the hook-and-mesh fastener securing second end 130 of cable 120 to distal portion 15 of brace body 10, in order to further fix second end 130 of cable 120 into place. Then proximal strap 50 is wrapped around the biceps portion of brace body 10 in order to further secure brace body 10 to the wearer.

As a result, when the elbow thereafter moves to full extension, cable 120 is tightened, whereby to apply a distal-to-proximal force on the elbow, and to apply a stabilizing force on the ulnar collateral ligament (UCL); and when the elbow thereafter moves to flexion, cable 120 is relaxed, so that the forces applied to the elbow by cable 120 are also relaxed.

Alternative Constructions

Figure 7:
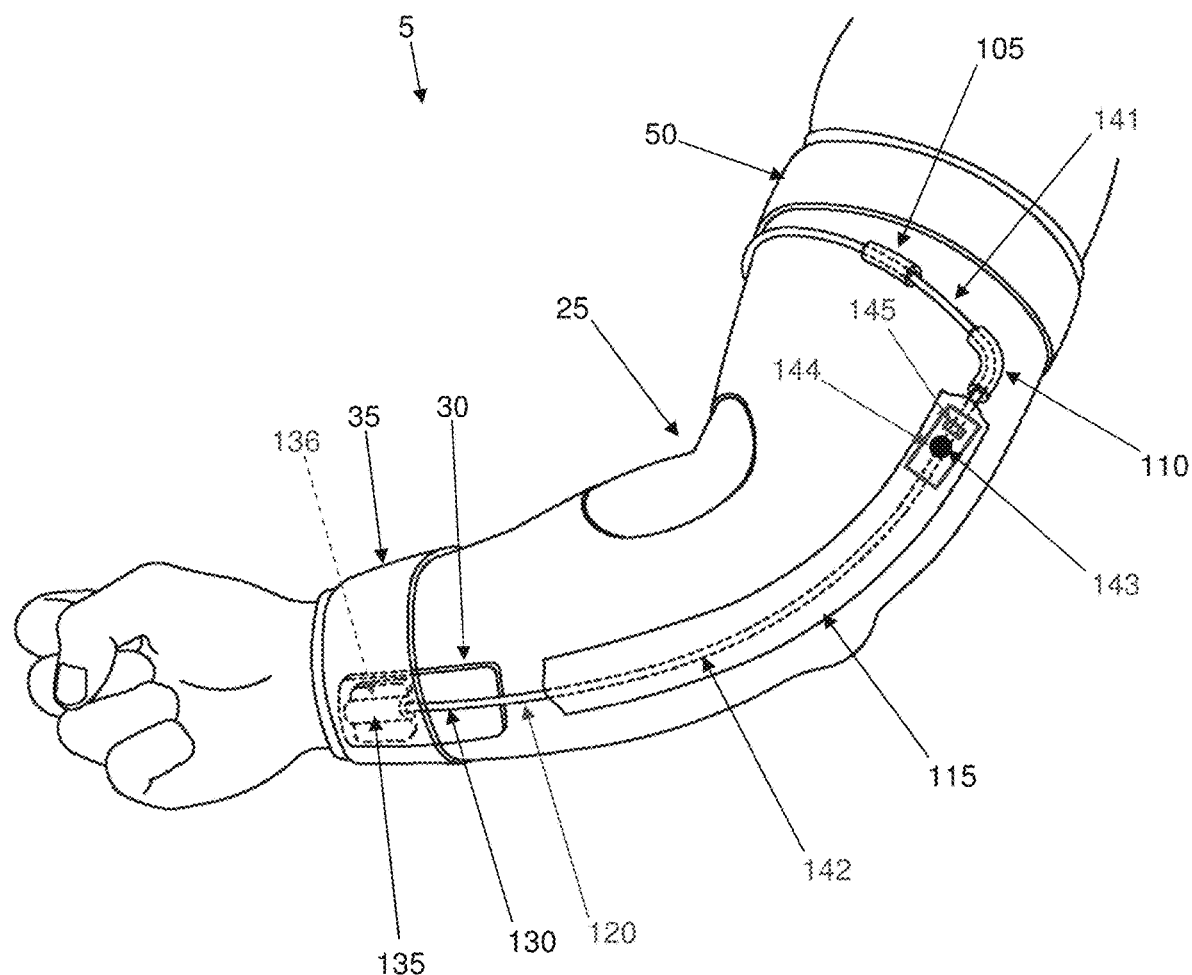
Figure 7A:
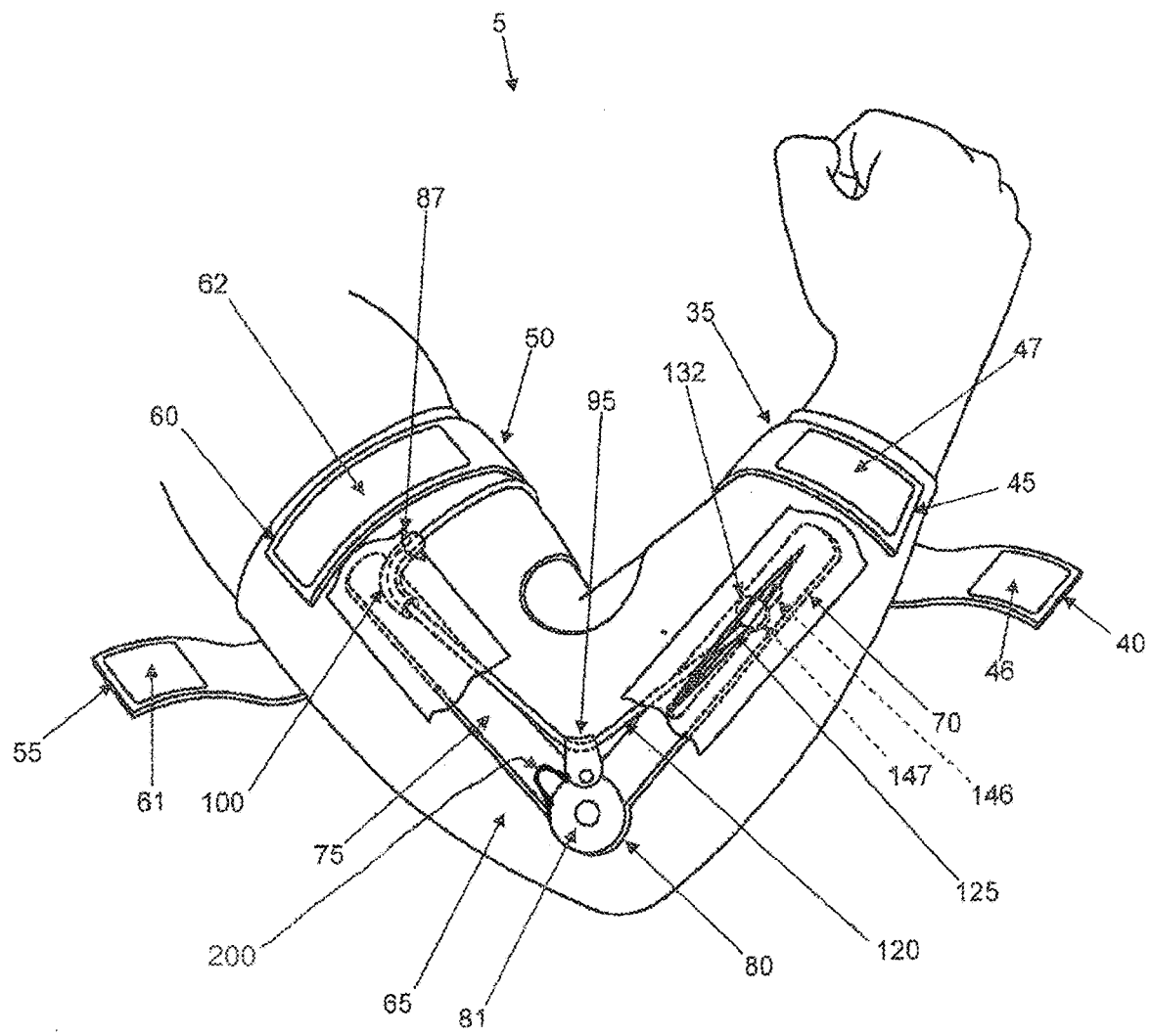
FIGS. 7A and 7B are schematic views showing another anatomical brace formed in accordance with the present invention.
Figure 7B:
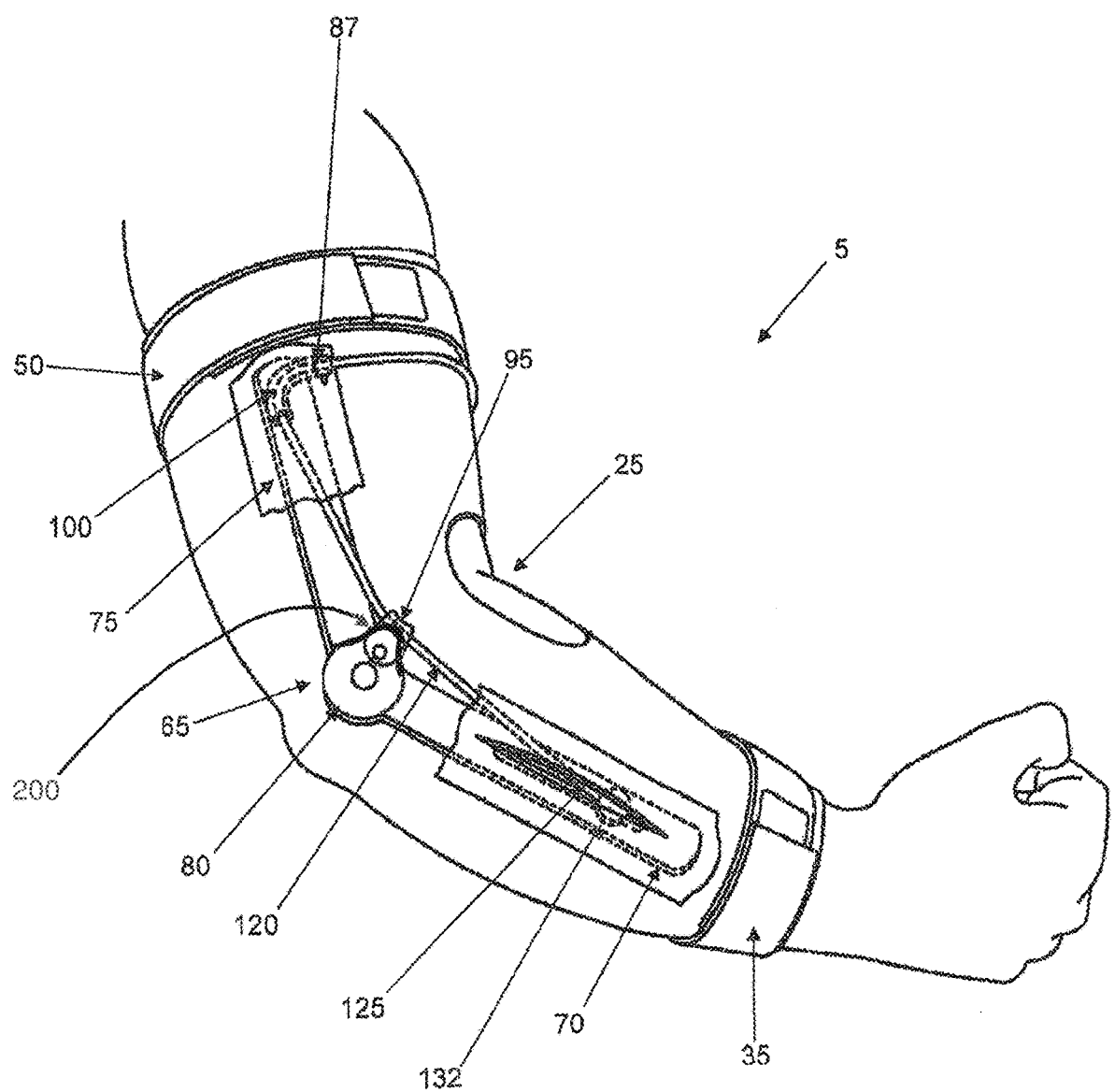

In one alternative form the invention, an offset cam may be provided at pivot 80 of hinge mechanism 65 so as to allow for greater tensioning of cable 120 during elbow extension and greater unloading of the tension during elbow flexion. See, for example, FIGS. 7A and 7B, which show a cam 200 located at pivot 80: cam 200 allows for greater tensioning of cable 120 during elbow extension (i.e., during transition from the position of FIG. 7A to the position of FIG. 7B) and greater unloading of the tension during elbow flexion (i.e., during transition from the position of FIG. 7B to the position of FIG. 7A).

Figure 8:
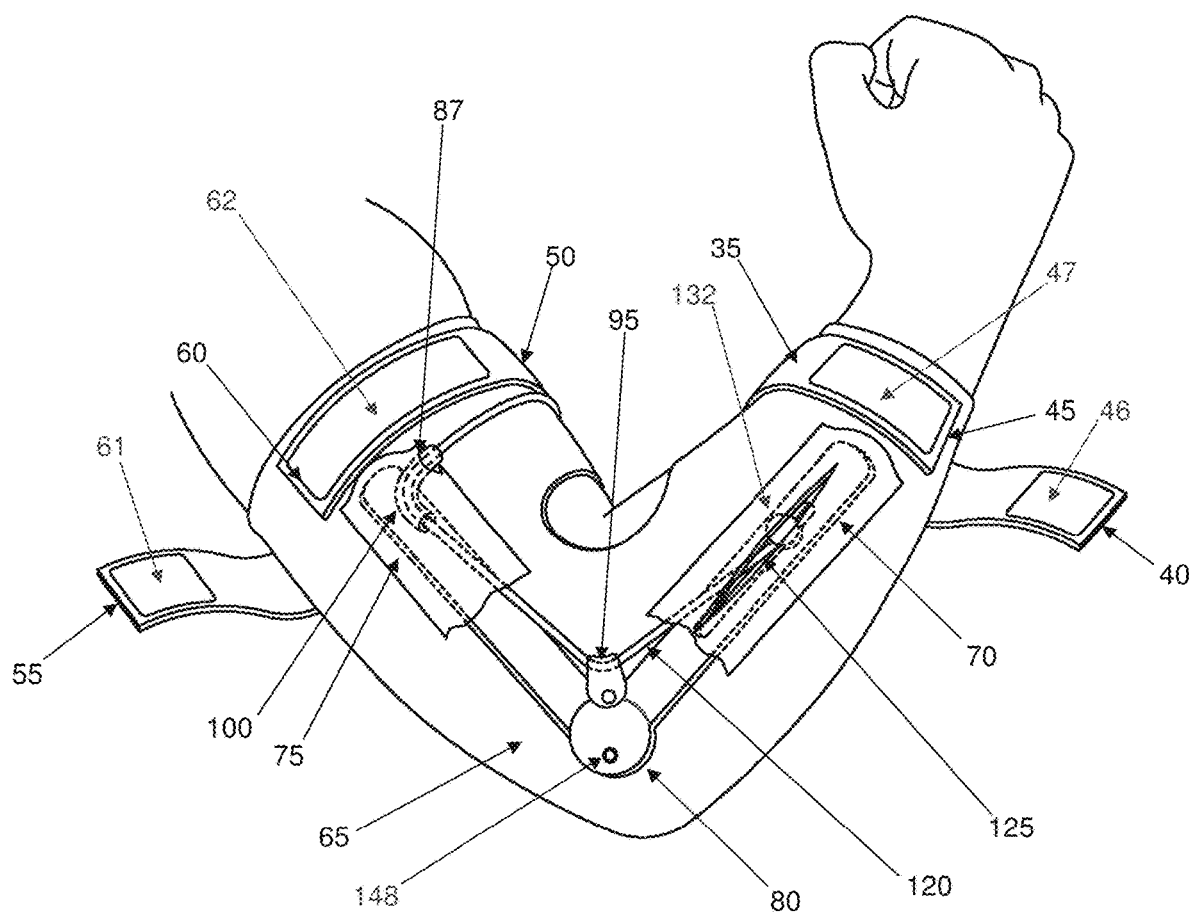
FIG. 8 is a schematic view showing still another anatomical brace formed in accordance with the present invention.
Figure 9:
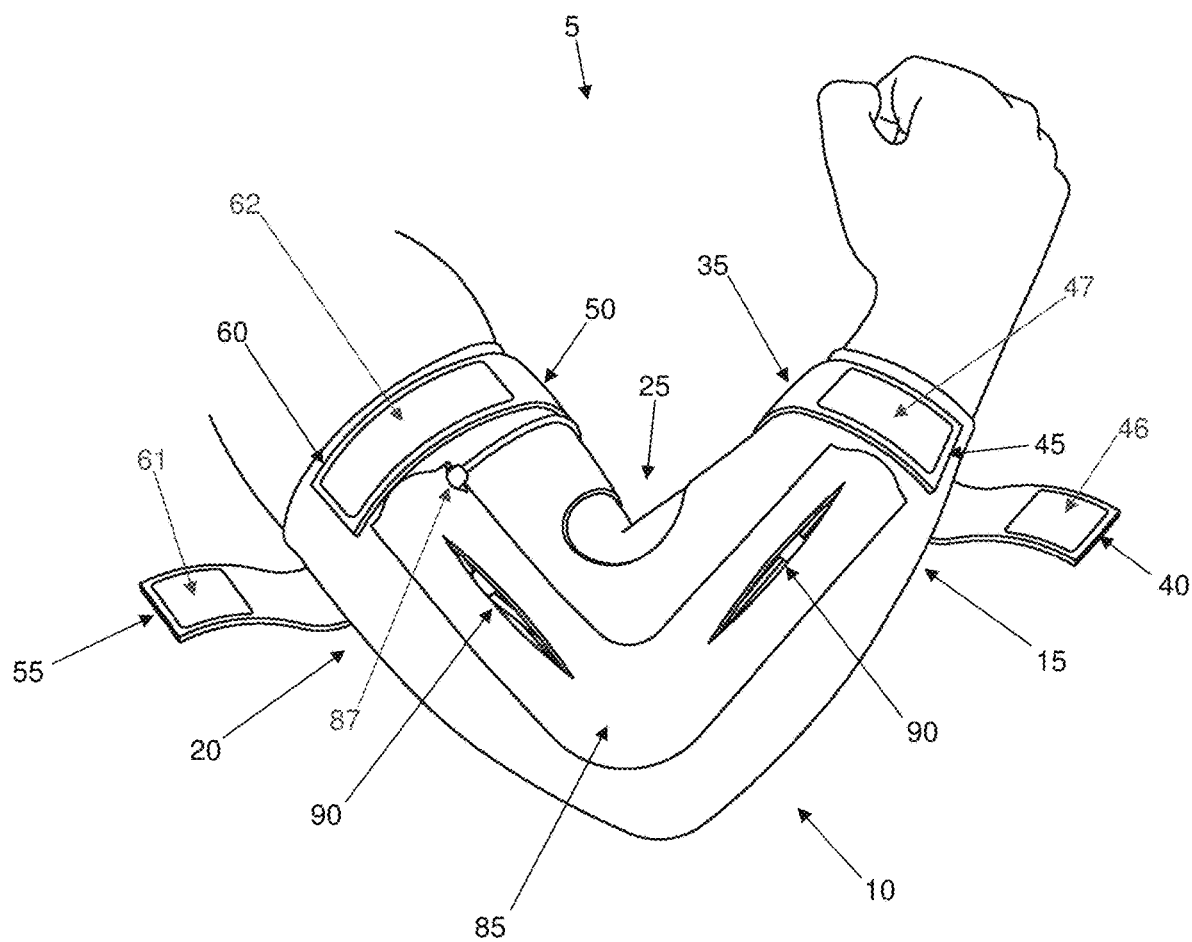
FIGS. 9-14 are schematic views showing yet another anatomical brace formed in accordance with the present invention.
Figure 10:
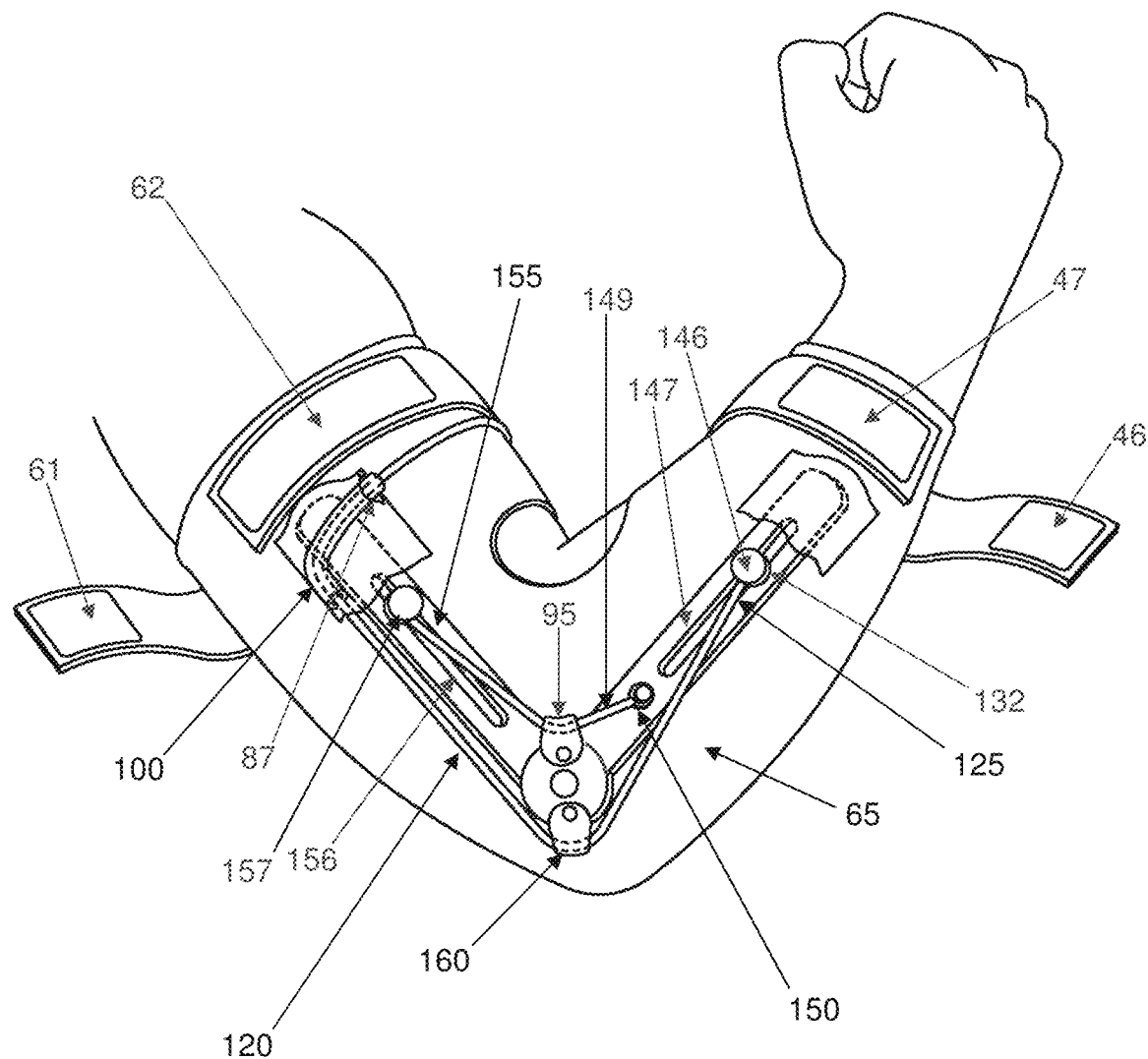
Figure 11:
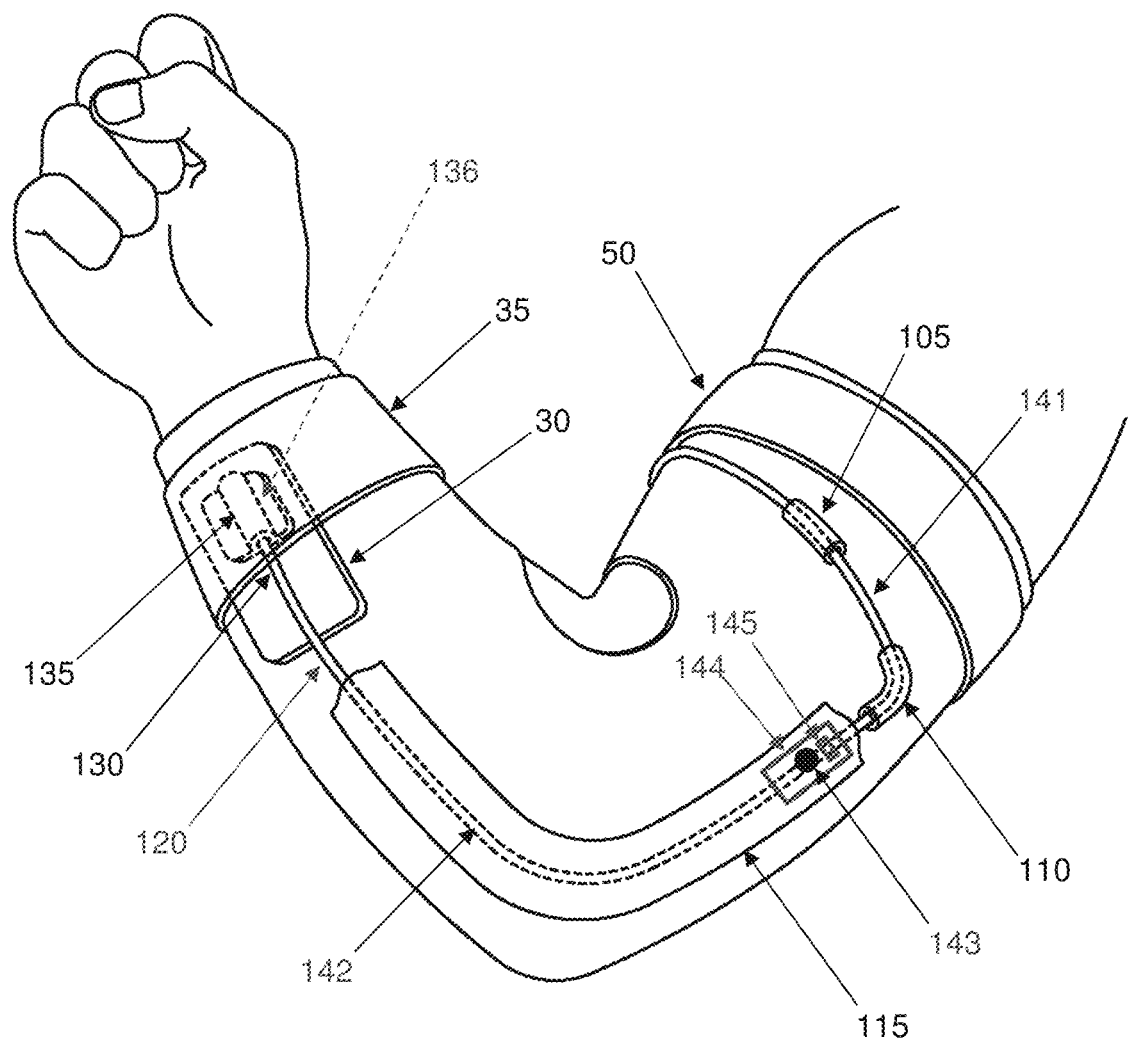
Figure 12:
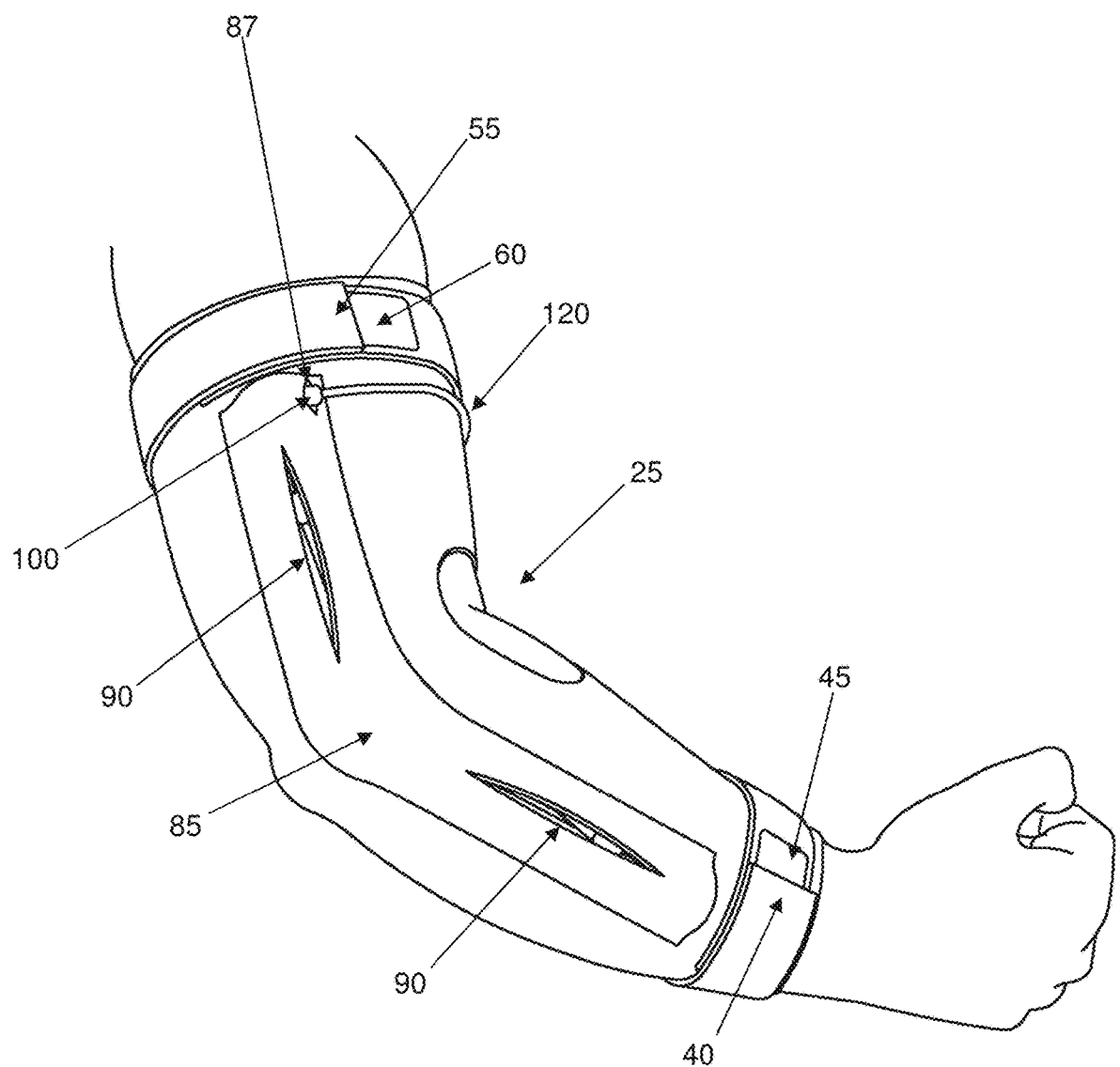
Figure 13:
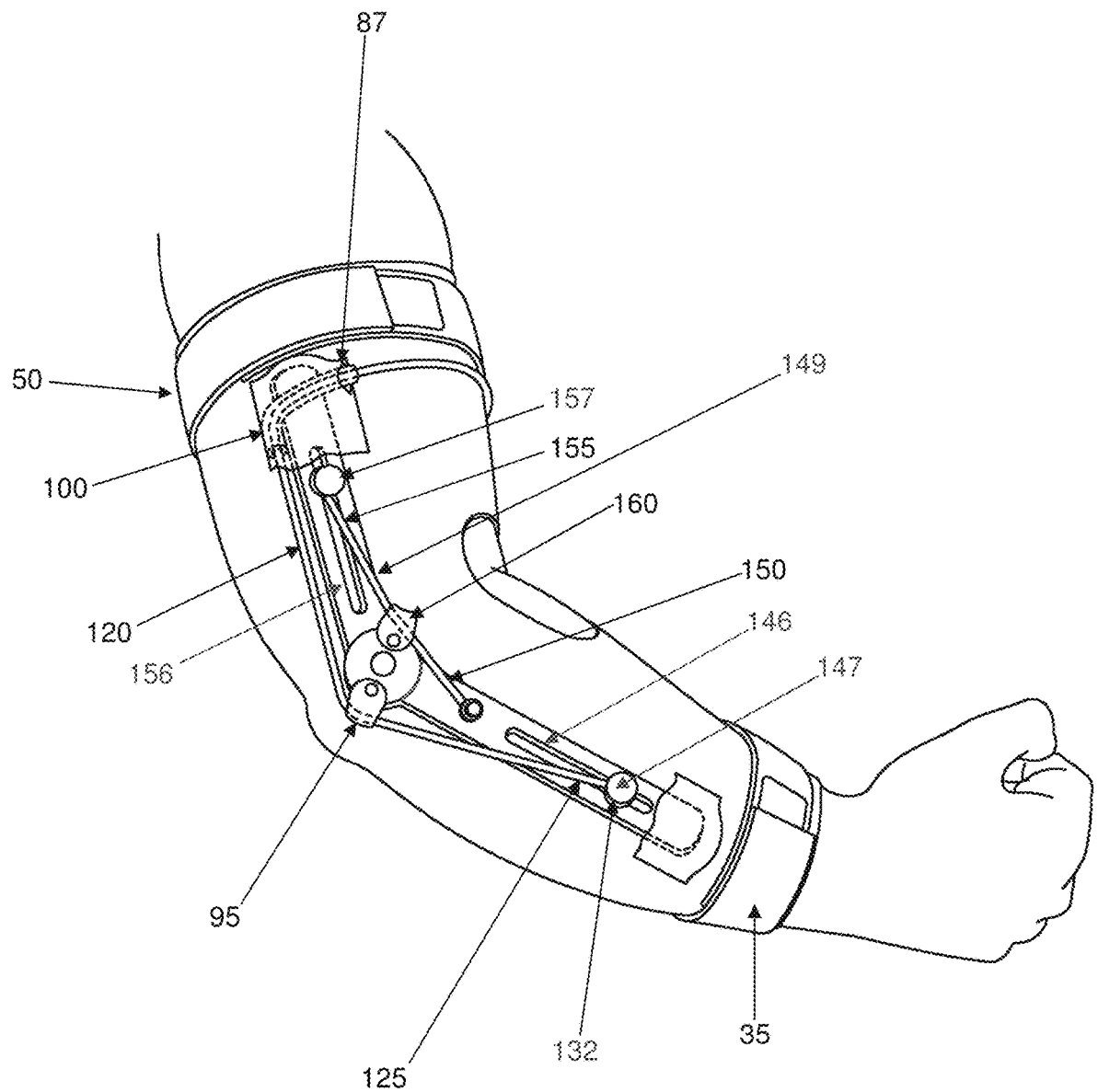
Figure 14:
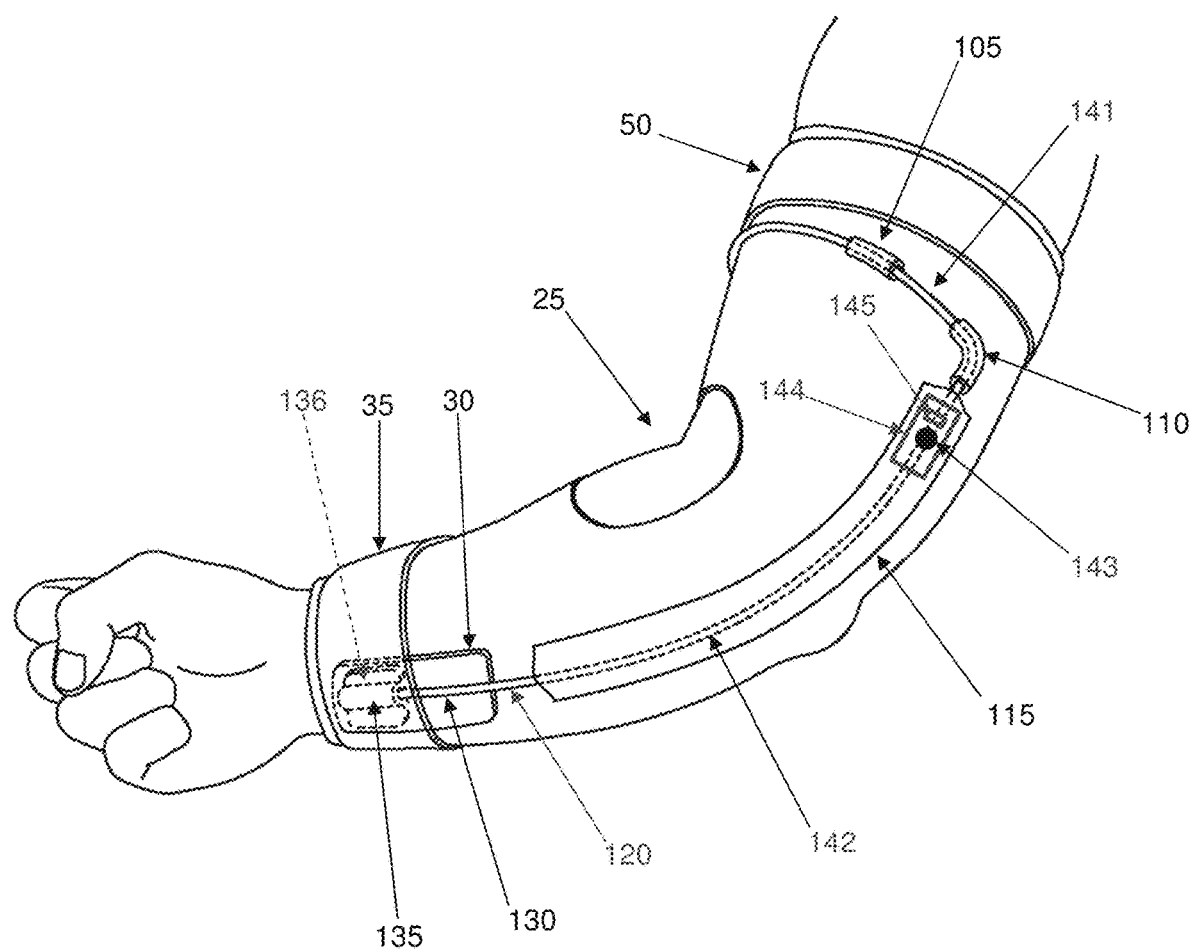

In a similar way, and looking now at FIG. 8, there is shown an alternative anatomical brace 5 which provides increased mechanical advantage during the cocking and acceleration phases of throwing (or during other activities involving elbow flexion and extension). This form of the anatomical brace is generally similar to the anatomical brace shown in FIGS. 2-7, except that pivot 80 of hinge mechanism 65 comprises an off-center pivot point 148. More particularly, off-center pivot point 148 modifies the path of cable 120 during articulation of the elbow in order to provide increased mechanical advantage during the cocking and acceleration phases of throwing (or during other activities involving elbow flexion and extension).

In another alternative form of the invention, second cable guide 100 of anatomical brace 5 may be configured conversely, so that cable 120 is directed laterally across the posterior triceps area (rather than laterally across the anterior biceps area.

In another alternative form of the invention, hinge mechanism 65 of anatomical brace 5 may be placed on the ulnar side of the elbow, with cable 120 running along the radial side of the elbow.

And in another alternative form of the invention, and looking now at FIGS. 9-14, there is shown an alternative anatomical brace 5 which provides additional ulnar collateral ligament (UCL) protection and additional throwing power through the acceleration phase of throwing (or additional extension power through the acceleration phase of elbow extension). This form of the anatomical brace is generally similar to the anatomical brace shown in FIGS. 2-7, except that the anatomical brace comprises a second limiter cable 149, and the aforementioned cable 120 is routed differently around pivot 80.

More particularly, second limiter cable 149 comprises a first end 150 which is fixed to distal segment 70 of hinge mechanism 65, and a second end 155 which is adjustably secured to proximal segment 75 of hinge mechanism 65 (e.g., via a rail 156 and a fixation element (e.g., a set screw) 157). The intermediate portion of second limiter cable 149 passes through the aforementioned first cable guide 95. Second limiter cable 149 is formed out of an inelastic material. In essence, second limiter cable 149 is configured to prevent full extension of the elbow of a wearer, thus providing additional protection to a wearer from injuries due to overextension of the elbow. The extent of extension permitted by second limiter cable 149 is set by the length of second limiter cable 149 and the point at which second limiter cable 149 is secured to proximal segment 75 of hinge mechanism 65.

In this form of the invention, cable 120 still comprises an inelastic first segment 141 and an elastic second segment 142, with inelastic first segment 141 transitioning to elastic second segment 142 at transition zone 143. However, in this form of the invention, inelastic first segment 141 of cable 120 runs through a cable guide 160 set along the posterior aspect of hinge mechanism 65. This construction still allows for tightening of cable 120 during elbow flexion and loosening of cable 120 during elbow extension. The tensioning during elbow flexion will provide increased tension along the ulnar side of the elbow to further protect the ulnar collateral ligament (UCL) against extreme valgus forces during elbow flexion. This construction will also provide a wearer with additional power through the acceleration phase of throwing (or other elbow extension) as the elastic component of cable 120 provides a mechanical force (i.e., a mechanical advantage) to help pull the forearm forward, whereby to increase acceleration and increase throwing (or other elbow extension) power and velocity.

With this dual cable construction (i.e., one cable 149 anterior to pivot 80 and one cable 120 posterior to pivot 80), anatomical brace 5 is designed to provide both superior protection of the ulnar collateral ligament (UCL) and increased throwing power during the cocking and acceleration phases of throwing (or other activities which involve elbow extension), as well as protecting the elbow from overextension during the release and follow-through phases of throwing (or other activities which involve elbow extension). Additionally, each cable can be adjusted independently of the other so as to maximize functionality and to be most specific to the individual needs of a wearer.

Figure 15:
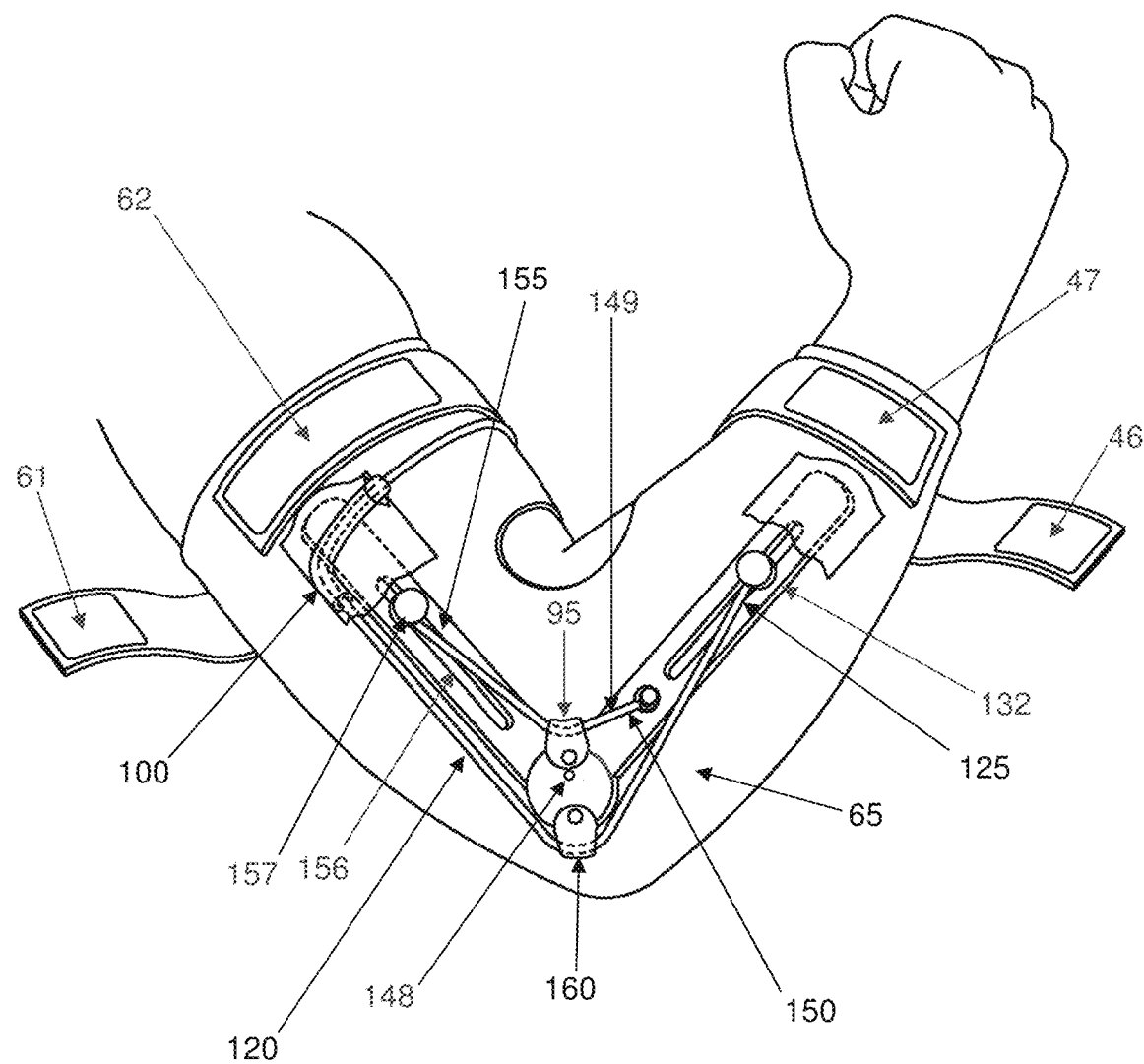
FIG. 15 is a schematic view showing another anatomical brace formed in accordance with the present invention.

It should also be appreciated that the anatomical brace shown in FIGS. 9-14 may also have an off-center pivot point construction (see, for example, FIG. 15).

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. An anatomical brace for dynamically stabilizing the elbow during elbow articulation, said anatomical brace comprising:
   a brace body comprising a distal portion for fitting over the forearm of a user and a proximal portion for fitting over the upper arm of a user;
   a hinge mechanism comprising a distal segment, a proximal segment and a pivot for pivotally connecting said distal segment and said proximal segment, said distal segment of said hinge mechanism being mounted to said distal portion of said brace body and said proximal segment of said hinge mechanism being mounted to said proximal portion of said brace body;
a pivot cable guide mounted to the anterior portion of said pivot;
an upper arm cable guide mounted to at least one of said proximal segment of said hinge mechanism and said proximal portion of said brace body, said upper arm cable guide being configured to change the direction of a cable extending through said upper arm cable guide;
an ulnar collateral ligament (UCL) cable guide mounted to said brace body and configured to direct a cable extending through said ulnar collateral ligament (UCL) cable guide over the ulnar collateral ligament (UCL) and toward said distal portion of said brace body; and
a cable having a first end and a second end;
said first end of said cable being mounted to said distal segment of said hinge mechanism, said second end of said cable being mounted to said distal portion of said brace body, and said cable being routed proximally along said distal segment of said hinge mechanism, through said pivot cable guide, proximally along said proximal segment of said hinge mechanism, through said upper arm cable guide, and through said ulnar collateral ligament (UCL) cable guide;
wherein, when said anatomical brace is mounted to the arm of a user so that said distal portion of said brace body is secured to the forearm of the user, and said proximal portion of said brace body is secured to the upper arm of the user, and when the elbow thereafter moves to full extension, said cable is tensioned, whereby to apply a force to the ulnar collateral ligament (UCL) of the user, and when the elbow thereafter moves to full flexion, said cable is relaxed, so that the force applied to the ulnar collateral ligament (UCL) is released.

2. An anatomical brace according to claim 1 wherein said cable comprises a non-elastic first segment and an elastic second segment.

3. An anatomical brace according to claim 2 wherein said non-elastic first segment is mounted to said distal segment of said hinge mechanism, and said elastic second segment is mounted to said distal portion of said brace body.

4. An anatomical brace according to claim 3 wherein said non-elastic first segment is connected to said elastic second segment with a connector, such that said elastic second segment can be replaced by another elastic second segment having different attributes.

5. An anatomical brace according to claim 4 wherein said different attributes comprise at least one from the group consisting of elasticity and tensile strength.

6. An anatomical brace according to claim 5 wherein said connector comprises a tension sensor for detecting the tension at said connector.

7. An anatomical brace according to claim 6 wherein said tension sensor is configured to communicate the tension detected at said connector to another device.

8. An anatomical brace according to claim 7 wherein said tension sensor is configured to wirelessly communicate the tension detected at said connector to another device.

9. An anatomical brace according to claim 7 wherein said another device comprises one from the group consisting of a smartphone, a smartwatch, a tablet and a laptop.

10. An anatomical brace according to claim 1 wherein said brace body comprises a tube.

11. An anatomical brace according to claim 10 wherein said tube is formed out of a flexible material selected from the group consisting of a woven fabric and a synthetic rubber.

12. An anatomical brace according to claim 11 wherein an opening is formed in said tube in the region of the antecubital area.

13. An anatomical brace according to claim 1 wherein said first end of said cable is adjustably mounted to said distal segment of said hinge mechanism.

14. An anatomical brace according to claim 13 wherein said first end of said cable is adjustably mounted to said distal segment of said hinge mechanism by means of a rail and a fixation element.

15. An anatomical brace according to claim 1 wherein said second end of said cable is adjustably mounted to said distal portion of said brace body.

16. An anatomical brace according to claim 15 wherein said second end of said cable is adjustably mounted to said distal portion of said brace body by means of a hook-and-mesh fastener.

17. An anatomical brace according to claim 1 wherein said pivot comprises an offset cam for increasing tensioning of said cable during elbow extension and increasing unloading of the tension during elbow flexion.

18. An anatomical brace according to claim 1 wherein said pivot comprises an off-center pivot point for increasing tensioning of said cable during elbow extension and increasing unloading of the tension during elbow flexion.

19. An anatomical brace for dynamically stabilizing the elbow during elbow articulation, said anatomical brace comprising:
a brace body comprising a distal portion for fitting over the forearm of a user and a proximal portion for fitting over the upper arm of a user;
a hinge mechanism comprising a distal segment, a proximal segment and a pivot for pivotally connecting said distal segment and said proximal segment, said distal segment of said hinge mechanism being mounted to said distal portion of said brace body and said proximal segment of said hinge mechanism being mounted to said proximal portion of said brace body;
a pivot cable guide mounted to the posterior portion of said pivot;
an upper arm cable guide mounted to at least one of said proximal segment of said hinge mechanism and said proximal portion of said brace body, said upper arm cable guide being configured to change the direction of a cable extending through said upper arm cable guide;
an ulnar collateral ligament (UCL) cable guide mounted to said brace body and configured to direct a cable extending through said ulnar collateral ligament (UCL) cable guide over the ulnar collateral ligament (UCL) and toward said distal portion of said brace body;
a cable having a first end and a second end;
said first end of said cable being mounted to said distal segment of said hinge mechanism, said second end of said cable being mounted to said distal portion of said brace body, and said cable being routed proximally along said distal segment of said hinge mechanism, through said pivot cable guide, proximally along said proximal segment of said hinge mechanism, through said upper arm cable guide, and through said ulnar collateral ligament (UCL) cable guide;
a limiter cable guide mounted to the anterior portion of said pivot; and
a limiter cable having a first end and a second end;

said first end of said limiter cable being mounted to said distal segment of said hinge mechanism, said second end of said limiter cable being mounted to said proximal segment of said hinge mechanism, and said limiter cable being routed through said limiter cable guide;

wherein, when said anatomical brace is mounted to the arm of a user so that said distal portion of said brace body is secured to the forearm of the user, and said proximal portion of said brace body is secured to the upper arm of the user, and when the elbow thereafter moves to full extension, said cable is tensioned, whereby to apply a force to the ulnar collateral ligament (UCL) of the user, and when the elbow thereafter moves to full flexion, said cable is relaxed, so that the force applied to the ulnar collateral ligament (UCL) is released.

20. A method for dynamically stabilizing the elbow during elbow articulation, said method comprising:

providing an anatomical brace, said anatomical brace comprising:
- a brace body comprising a distal portion for fitting over the forearm of a user and a proximal portion for fitting over the upper arm of a user;
- a hinge mechanism comprising a distal segment, a proximal segment and a pivot for pivotally connecting said distal segment and said proximal segment, said distal segment of said hinge mechanism being mounted to said distal portion of said brace body and said proximal segment of said hinge mechanism being mounted to said proximal portion of said brace body;
- a pivot cable guide mounted to the anterior portion of said pivot;
- an upper arm cable guide mounted to at least one of said proximal segment of said hinge mechanism and said proximal portion of said brace body, said upper arm cable guide being configured to change the direction of a cable extending through said upper arm cable guide;
- an ulnar collateral ligament (UCL) cable guide mounted to said brace body and configured to direct a cable extending through said ulnar collateral ligament (UCL) cable guide over the ulnar collateral ligament (UCL) and toward said distal portion of said brace body; and
- a cable having a first end and a second end;

said first end of said cable being mounted to said distal segment of said hinge mechanism, said second end of said cable being mounted to said distal portion of said brace body, and said cable being routed proximally along said distal segment of said hinge mechanism, through said pivot cable guide, proximally along said proximal segment of said hinge mechanism, through said upper arm cable guide, and through said ulnar collateral ligament (UCL) cable guide;

wherein, when said anatomical brace is mounted to the arm of a user so that said distal portion of said brace body is secured to the forearm of the user, and said proximal portion of said brace body is secured to the upper arm of the user, and when the elbow thereafter moves to full extension, said cable is tensioned, whereby to apply a force to the ulnar collateral ligament (UCL) of the user, and when the elbow thereafter moves to full flexion, said cable is relaxed, so that the force applied to the ulnar collateral ligament (UCL) is released;

fitting said distal portion of said brace body over the forearm of a user and said proximal portion of said brace body over the upper arm of a user;

positioning said first end of said cable to said distal segment of said hinge mechanism, and positioning said second end of said cable to said distal portion of said brace body; and articulating the elbow.

21. A method according to claim 20:
wherein said cable comprises a non-elastic first segment and an elastic second segment;
wherein said non-elastic first segment is mounted to said distal segment of said hinge mechanism, and said elastic second segment is mounted to said distal portion of said brace body;
wherein said non-elastic first segment is connected to said elastic second segment with a connector;
and further wherein after articulating the elbow, said elastic second segment is replaced by another elastic second segment having different attributes.

22. A method according to claim 21 wherein said connector comprises a tension sensor for detecting the tension at said connector, and further wherein said elastic second segment is replaced by another elastic second segment having different attributes after said tension sensor detects a tension.

23. A method for dynamically stabilizing the elbow during elbow articulation, said method comprising:

providing an anatomical brace, said anatomical brace comprising:
- a brace body comprising a distal portion for fitting over the forearm of a user and a proximal portion for fitting over the upper arm of a user;
- a hinge mechanism comprising a distal segment, a proximal segment and a pivot for pivotally connecting said distal segment and said proximal segment, said distal segment of said hinge mechanism being mounted to said distal portion of said brace body and said proximal segment of said hinge mechanism being mounted to said proximal portion of said brace body;
- a pivot cable guide mounted to the posterior portion of said pivot;
- an upper arm cable guide mounted to at least one of said proximal segment of said hinge mechanism and said proximal portion of said brace body, said upper arm cable guide being configured to change the direction of a cable extending through said upper arm cable guide;
- an ulnar collateral ligament (UCL) cable guide mounted to said brace body and configured to direct a cable extending through said ulnar collateral ligament (UCL) cable guide over the ulnar collateral ligament (UCL) and toward said distal portion of said brace body;
- a cable having a first end and a second end;

said first end of said cable being mounted to said distal segment of said hinge mechanism, said second end of said cable being mounted to said distal portion of said brace body, and said cable being routed proximally along said distal segment of said hinge mechanism, through said pivot cable guide, proximally along said proximal segment of said hinge mechanism, through said upper arm cable guide, and through said ulnar collateral ligament (UCL) cable guide;

a limiter cable guide mounted to the anterior portion of said pivot; and a limiter cable having a first end and a second end;

said first end of said limiter cable being mounted to said distal segment of said hinge mechanism, said second end of said limiter cable being mounted to said proximal segment of said hinge mechanism, and said limiter cable being routed through said limiter cable guide;

wherein, when said anatomical brace is mounted to the arm of a user so that said distal portion of said brace body is secured to the forearm of the user, and said proximal portion of said brace body is secured to the upper arm of the user, and when the elbow thereafter moves to full extension, said cable is tensioned, whereby to apply a force to the ulnar collateral ligament (UCL) of the user, and when the elbow thereafter moves to full flexion, said cable is relaxed, so that the force applied to the ulnar collateral ligament (UCL) is released;

fitting said distal portion of said brace body over the forearm of a user and said proximal portion of said brace body over the upper arm of a user;

positioning said first end of said cable to said distal segment of said hinge mechanism, and positioning said second end of said cable to said distal portion of said brace body, and positioning said first end of said limiter cable to said distal segment of said hinge mechanism, and positioning said second end of said limiter cable to said proximal segment of said hinge mechanism; and articulating the elbow.

\* \* \* \* \*